United States Patent
Modlin et al.

(10) Patent No.: US 6,326,605 B1
(45) Date of Patent: Dec. 4, 2001

(54) BROAD RANGE LIGHT DETECTION SYSTEM

(75) Inventors: Douglas N. Modlin, Palo Alto; David P. Stumbo, Belmont; Rick V. Stellmacher, San Jose, all of CA (US)

(73) Assignee: LJL Biosystems, Inc., Sunnyvale, CA (US)

( * ) Notice: Subject to any disclaimer, the term of this patent is extended or adjusted under 35 U.S.C. 154(b) by 0 days.

(21) Appl. No.: 09/643,221

(22) Filed: Aug. 18, 2000

Related U.S. Application Data

(63) Continuation of application No. PCT/US99/03678, filed on Feb. 19, 1999, and a continuation of application No. PCT/US98/23095, filed on Oct. 30, 1998, and a continuation of application No. 09/160,533, filed on Sep. 24, 1998, now Pat. No. 6,097,025, and a continuation of application No. 09/062,472, filed on Apr. 17, 1998, now Pat. No. 6,071,748, application No. 09/643,221, which is a continuation of application No. PCT/US99/01656, filed on Jan. 25, 1999.

(60) Provisional application No. 60/100,951, filed on Sep. 18, 1998, provisional application No. 60/082,253, filed on Apr. 17, 1998, and provisional application No. 60/075,414, filed on Feb. 20, 1998.

(51) Int. Cl.[7] .................................................. H01J 40/14
(52) U.S. Cl. .............................. 250/214 SW; 250/214 R
(58) Field of Search ........................ 250/214 SW, 214 R, 250/205, 214.1, 206, 223 R, 221, 227.22, 227.11; 356/73; 327/564, 565

(56) References Cited

U.S. PATENT DOCUMENTS

| | | |
|---|---|---|
| 2,719,214 | 9/1955 | Potter . |
| 3,013,467 | 12/1961 | Minsky . |
| 3,423,581 | 1/1969 | Baer . |
| 3,516,736 | 6/1970 | Weaver . |
| 3,849,654 | 11/1974 | Malvin . |
| 3,885,162 | 5/1975 | Geertz . |
| 3,932,023 | 1/1976 | Humer . |
| 4,011,451 | 3/1977 | Nelson . |
| 4,067,653 | 1/1978 | Fletcher et al. . |
| 4,074,939 | 2/1978 | Rabl . |
| 4,076,420 | 2/1978 | Maeyer et al. . |
| 4,100,416 | 7/1978 | Hirschfeld . |
| 4,144,452 | 3/1979 | Harte . |
| 4,150,870 | 4/1979 | d' Auria . |

(List continued on next page.)

FOREIGN PATENT DOCUMENTS

| | | |
|---|---|---|
| 0 222 341 A1 | 5/1987 | (EP) . |
| 0 266 881 A2 | 5/1988 | (EP) . |
| 0 259 386 B1 | 4/1991 | (EP) . |

(List continued on next page.)

OTHER PUBLICATIONS

*Standard Handbook for Electrical Engineers*, Fink et al., pp. 22–2 through 25–5 (11th ed. 1978) (Month Unknown).

*Fundamentals of Light Microscopy*, Spencer, Cambridge University Press, 1982. (Month Unknown).

Joseph R. Lakowicz, *Principles of Fluorescence Spectroscopy*, First Edition, Sep. 1983.

(List continued on next page.)

Primary Examiner—Que T. Le
(74) Attorney, Agent, or Firm—Kolisch, Hartwell, Dickinson, McCormack & Heuser, PC

(57) ABSTRACT

A broad-range light-detection system. In some embodiments, the system includes apparatus and methods for detecting light with high accuracy over a broad range of intensities. In other embodiments, the system includes apparatus and methods for automatically scaling the detection range to improve detection based on the intensity of the detected light. In yet other embodiments, the system includes apparatus and methods for detecting light with increased speed, particularly in applications involving analysis of successive samples.

8 Claims, 11 Drawing Sheets

U.S. PATENT DOCUMENTS

| | | |
|---|---|---|
| 4,203,670 | 5/1980 | Bromberg . |
| 4,240,751 | 12/1980 | Linnecke et al. . |
| 4,296,326 | 10/1981 | Haslop et al. . |
| 4,397,560 | 8/1983 | Andersen . |
| 4,451,149 | 5/1984 | Noeller . |
| 4,451,433 | 5/1984 | Yamashita et al. . |
| 4,485,430 | 11/1984 | Fustel . |
| 4,501,970 | 2/1985 | Nelson . |
| 4,567,847 | 2/1986 | Linner . |
| 4,591,550 | 5/1986 | Hafeman et al. . |
| 4,626,684 | 12/1986 | Landa . |
| 4,646,214 | 2/1987 | Mendleski . |
| 4,685,801 | 8/1987 | Minekane . |
| 4,699,512 | 10/1987 | Koshi . |
| 4,704,255 | 11/1987 | Jolley . |
| 4,707,067 | 11/1987 | Haberland et al. . |
| 4,730,921 | 3/1988 | Klein et al. . |
| 4,737,464 | 4/1988 | McConnell et al. . |
| 4,738,825 | 4/1988 | Kelln et al. . |
| 4,741,619 | 5/1988 | Humphries et al. . |
| 4,753,501 | 6/1988 | Battle . |
| 4,758,786 | 7/1988 | Hafeman . |
| 4,762,420 | 8/1988 | Bowley . |
| 4,772,453 | 9/1988 | Lisenbee . |
| 4,784,275 | 11/1988 | Fridge . |
| 4,802,768 | 2/1989 | Gifford et al. . |
| 4,808,828 | 2/1989 | Kitamori et al. . |
| 4,810,096 | 3/1989 | Russell et al. . |
| 4,826,660 | 5/1989 | Smith et al. . |
| 4,855,930 | 8/1989 | Chao et al. . |
| 4,868,103 | 9/1989 | Stavrianopoulos et al. . |
| 4,873,633 | 10/1989 | Mezei et al. . |
| 4,877,965 | 10/1989 | Dandliker et al. . |
| 4,885,087 | 12/1989 | Kopf . |
| 4,892,409 | 1/1990 | Smith . |
| 4,897,548 | 1/1990 | Döme et al. . |
| 4,923,819 | 5/1990 | Fernandez et al. . |
| 4,931,402 | 6/1990 | Abplanalp . |
| 4,936,682 | 6/1990 | Hoyt . |
| 4,948,442 | 8/1990 | Manns . |
| 4,963,815 | 10/1990 | Hafeman . |
| 4,968,148 | 11/1990 | Chow et al. . |
| 4,979,821 | 12/1990 | Schutt et al. . |
| 5,001,725 * | 3/1991 | Senderwicz et al. ............... 375/28 |
| 5,009,488 | 4/1991 | Fay et al. . |
| 5,018,866 | 5/1991 | Osten . |
| 5,020,995 | 6/1991 | Levy . |
| 5,034,613 | 7/1991 | Denk et al. . |
| 5,039,219 | 8/1991 | James et al. . |
| 5,047,215 | 9/1991 | Manns . |
| 5,058,045 | 10/1991 | Ma . |
| 5,082,628 | 1/1992 | Andreotti et al. . |
| 5,084,246 | 1/1992 | Lyman et al. . |
| 5,091,652 | 2/1992 | Mathies et al. . |
| 5,095,517 | 3/1992 | Monguzzi et al. . |
| 5,096,807 | 3/1992 | Leaback . |
| 5,164,319 | 11/1992 | Ohta et al. . |
| 5,169,601 | 12/1992 | Ohta et al. . |
| 5,192,510 | 3/1993 | Zoha et al. . |
| 5,196,709 | 3/1993 | Berndt et al. . |
| 5,198,670 | 3/1993 | VanCauter et al. . |
| 5,206,568 | 4/1993 | Björnson et al. . |
| 5,208,161 | 5/1993 | Saunders et al. . |
| 5,208,651 | 5/1993 | Buican . |
| 5,216,488 | 6/1993 | Tuunanen et al. . |
| 5,225,164 | 7/1993 | Astle . |
| 5,257,202 | 10/1993 | Fedderen et al. . |
| 5,270,788 | 12/1993 | Cercek et al. . |
| 5,273,718 | 12/1993 | Sköld et al. . |
| 5,275,951 | 1/1994 | Chow et al. . |
| 5,281,825 | 1/1994 | Berndt et al. . |
| 5,289,407 | 2/1994 | Strickler et al. . |
| 5,307,144 | 4/1994 | Hiroshi et al. . |
| 5,315,015 | 5/1994 | Hui et al. . |
| 5,317,485 | 5/1994 | Merjanian . |
| 5,319,436 | 6/1994 | Manns et al. . |
| 5,323,008 | 6/1994 | Studholme et al. . |
| 5,323,010 | 6/1994 | Gratton et al. . |
| 5,340,716 | 8/1994 | Ullman et al. . |
| 5,340,747 | 8/1994 | Eden . |
| 5,341,215 | 8/1994 | Seher . |
| 5,353,112 | 10/1994 | Smith . |
| 5,355,215 | 10/1994 | Schroeder et al. . |
| 5,357,095 | 10/1994 | Weyrauch et al. . |
| 5,361,626 | 11/1994 | Colligan et al. . |
| 5,384,093 | 1/1995 | Ootani et al. . |
| 5,401,465 | 3/1995 | Smethers et al. . |
| 5,418,371 | 5/1995 | Aslund et al. . |
| 5,420,408 | 5/1995 | Weyrauch et al. . |
| 5,436,718 | 7/1995 | Fernandes et al. . |
| 5,445,935 | 8/1995 | Royer . |
| 5,449,921 | 9/1995 | Baba . |
| 5,457,527 | 10/1995 | Manns et al. . |
| 5,459,300 | 10/1995 | Kasman . |
| 5,480,804 | 1/1996 | Niwa et al. . |
| 5,485,530 | 1/1996 | Lakowicz et al. . |
| 5,487,872 | 1/1996 | Hafeman et al. . |
| 5,491,343 | 2/1996 | Brooker . |
| 5,500,188 | 3/1996 | Hafeman et al. . |
| 5,504,337 | 4/1996 | Lakowicz et al. . |
| 5,512,492 | 4/1996 | Herron et al. . |
| 5,523,573 | 6/1996 | Hänninen et al. . |
| 5,527,684 | 6/1996 | Mabile et al. . |
| 5,528,046 | 6/1996 | Ishikawa . |
| 5,537,343 | 7/1996 | Kikinis et al. . |
| 5,541,113 | 7/1996 | Siddigi et al. . |
| 5,542,012 | 7/1996 | Fernandes et al. . |
| 5,557,398 | 9/1996 | Wechsler et al. . |
| 5,561,068 | 10/1996 | Rounbehler et al. . |
| 5,589,136 | 12/1996 | Northrup et al. . |
| 5,589,350 | 12/1996 | Bochner . |
| 5,589,351 | 12/1996 | Harootunian . |
| 5,592,289 | 1/1997 | Norris . |
| 5,593,867 | 1/1997 | Walker et al. . |
| 5,595,710 | 1/1997 | Van Dusen et al. . |
| 5,599,500 | 2/1997 | Jones . |
| 5,604,130 | 2/1997 | Warner et al. . |
| 5,620,894 | 4/1997 | Barger et al. . |
| 5,626,134 | 5/1997 | Zuckerman . |
| 5,631,734 | 5/1997 | Stern et al. . |
| 5,633,724 | 5/1997 | King et al. . |
| 5,635,402 | 6/1997 | Alfano et al. . |
| 5,641,633 | 6/1997 | Linn et al. . |
| 5,645,800 | 7/1997 | Masterson et al. . |
| 5,663,545 | 9/1997 | Marquiss . |
| 5,670,113 | 9/1997 | Akong et al. . |
| 5,672,880 | 9/1997 | Kain . |
| 5,676,943 | 10/1997 | Baetge et al. . |
| 5,677,196 | 10/1997 | Herron et al. . |
| 5,679,310 | 10/1997 | Manns . |
| 5,736,410 | 4/1998 | Zarling et al. . |
| 5,738,825 | 4/1998 | Rudigier et al. . |
| 5,741,554 | 4/1998 | Tisone . |
| 5,746,974 | 5/1998 | Massey et al. . |
| 5,750,410 | 5/1998 | Dou et al. . |
| 5,756,292 | 5/1998 | Royer . |
| 5,766,875 | 6/1998 | Hafeman et al. . |
| 5,780,857 | 7/1998 | Harju et al. . |
| 5,798,083 | 8/1998 | Massey et al. . |
| 5,798,085 | 8/1998 | Seaton et al. . |
| 5,825,617 | 10/1998 | Kochis et al. . |

| | | |
|---|---|---|
| 5,842,582 | 12/1998 | DeStefano, Jr. . |
| 5,888,454 | 3/1999 | Leistner et al. . |
| 5,905,571 | 5/1999 | Butler et al. . |
| 5,933,232 | 8/1999 | Atzler et al. . |
| 5,959,738 | 9/1999 | Hafeman et al. . |
| 5,989,835 | 11/1999 | Dunlay et al. . |
| 5,993,746 | 11/1999 | Priha et al. . |
| 6,020,591 | 2/2000 | Harter et al. . |
| 6,025,985 | 2/2000 | Leytes et al. . |
| 6,033,100 | 3/2000 | Marquiss et al. . |
| 6,071,748 | 6/2000 | Modlin et al. ................. 436/174 |
| 6,097,025 | 8/2000 | Modlin e tal. ................. 250/227.22 |
| 6,137,584 | 10/2000 | Seidel et al. ................. 356/445 |
| 6,159,425 | 12/2000 | Edwards et al. ................. 422/63 |
| 6,187,267 | 12/2000 | Taylor et al. ................. 422/52 |

FOREIGN PATENT DOCUMENTS

| | | |
|---|---|---|
| 0 977 037 A1 | 2/2000 | (EP) . |
| 0 993 916 A2 | 4/2000 | (EP) . |
| 0 995 555 A1 | 4/2000 | (EP) . |
| 1 003 020 A1 | 5/2000 | (EP) . |
| 1 003 039 A1 | 5/2000 | (EP) . |
| 2 215 838 A | 9/1989 | (GB) . |
| 2 228 081 A | 8/1990 | (GB) . |
| WO99/04288 | 1/1999 | (WO) . |
| WO 99/08233 | 2/1999 | (WO) . |
| WO99/23466 | 5/1999 | (WO) . |
| WO99/37203 | 7/1999 | (WO) . |
| WO99/42817 | 8/1999 | (WO) . |
| WO99/54711 | 10/1999 | (WO) . |
| WO00/04364 | 1/2000 | (WO) . |
| WO00/06989 | 2/2000 | (WO) . |
| WO00/06990 | 2/2000 | (WO) . |
| WO00/06991 | 2/2000 | (WO) . |
| WO00/42209 | 2/2000 | (WO) . |
| WO 00/50877 | 8/2000 | (WO) . |
| WO 00/55372 | 9/2000 | (WO) . |
| WO 00/66269 | 11/2000 | (WO) . |
| WO01/04608 | 1/2001 | (WO) . |

OTHER PUBLICATIONS

*Basic Fluorescence Microscopy*, Taylor et al., *Methods in Cell Biology*, vol. 29, pp. 207–237, 1989 (Month Unknown).
Quantitative Fluorescence Microscopy Using Photomultiplier Tubes and Imaging Detectors, Wampler et al., *Methods in Cell Biology*, vol. 29, pp. 239–267, 1989. (Month Unknown).
Three–Dimensional Confocal Fluorescence Microscopy, Brakenhoff et al., *Methods in Cell Biology*, vol. 30, pp. 379–389, 1989. (Month Unknown).
Laser Scanning Confocal Microscopy of Living Cells, Lemasters et al., *Optical Microscopy: Emerging Methods and Applications*, pp. 339–345, 1993. (Month Unknown).
Time–Resolved Fluorescence Lifetime Imaging, vandeVen et al., *Optical Microscopy: Emerging Methods and Applications*, pp. 373–389, 1993. (Month Unknown).
Electrochemiluminescence: A New Diagnostic and Research Tool, Yang et al., *Bio/Technology*, vol. 12, pp. 193–194, Feb. 1994.
High Throughput Screening Using Dynamic Fluorescence, Swift et al., *SPIE*, vol. 2388, pp. 182–189, Feb. 6–8, 1995.
Genesis Series Robotic Sample Processors brochure, Tecan AG, Oct. 1997.
Genesis Robotic Microplate Processor brochure, Tecan AG, Nov. 1997.
A Measure of Brilliance, TR717 Micrplate Luminometer brochure, Tropix, Inc., 1997. (Month Unknown).

Advanced Microplate Detection Systems brochure, Tecan AG, Feb. 1998.
The SPECTRA Family brocure, Tecan AG, Feb. 1998.
Assist Plate Handling Device brochure, Labsystems, May 1998.
Wallac Time–Resolved Fluorometry–The Key to Improved Assay Sensitivity, internet description pp., Jul. 7, 1998.
Wallac 1234 Delfia Fluorometer, internet description page, Jul. 7, 1998.
Wallac 1420 Victor Multilabel Counter, internet description pages, Jul. 7, 1998.
Wallac 1420 Victor$^2$ Multilabel Counter, internet description pages, Jul. 7, 1998.
Wallac 1442 Arthur Multi–Wavelenth Fluoroimager, internet description page, Jul. 7, 1998.
Wallac Labelling Reagents for Time–Resolved Fluorometry, internet description page, Jul. 7, 1998.
Genesis Assay Workstation brochure, Tecan AG, Jul. 1998.
Genesis Logistics Workstation brochure, Tecan AG, Jul. 1998.
Plarion brochure, Tecan AG, Aug. 1998.
CytoFluor Fluorescence Multi–Well Plate Reader brochure, PerSeptive Biosystems, 1998 (Month Unknown).
Fixed Polarizer Ellipsometry for Simple and Sensitive Detection of Thin Films Generated by Specific Molecular Interactions: Applications in Immunoassays and DNA Sequences Detection, Ostroff et al., *Clinical Chemistry*, vol. 44, No. 9, pp. 2031–2035, 1998. (Month Unknown).
Microplate Instrumentation Catalogue 1998, Labsystems, 1998. (Month Unknown).
Magellan, Instrument Control and Data Analysis Software brochure, Tecan AG, Nov. 1999.
Twister™, Tecan's Automated Micrplate Handler brochure, Tecan AG, Nov. 1999.
Absorbance Readers brochure, Tecan AG, Dec. 1999.
Ultra—The Solution for HTS and Assay Development brochure, Tecan Austria GmbH, Dec. 1999.
Joseph R. Lakowicz, *Principles of Fluorescence Spectroscopy*, Second Edition, 1999 (Month Unknown).
CyBi™–Lumax 1,536 brochure, CyBio AG, May 2000.
CyBi™–PlateSafe brochure, CyBio AG, May 2000.
SPECTRAmax® Gemini XS brochure, Molecular Devices Corp., Jun. 2000.
Packard BioScience Company Introduces the Fusion™ Universal Microplate Analyzer press release, Packard BioScience Company, Jun. 29, 2000.
SPECTRAmax® Plus$^{384}$ brochure, Molecular Devices Corp., Jun. 2000.
Labcyte: Research and Clinical Instruments for Life Sciences brochure, Arlena Research LLC, Aug. 1, 2000.
Fusion™, Universal Microplate Analyzer, Packard BioScience Company, Aug. 2000.
CyBi™–Screen–Machine: One System–Many Solutions brochure, CyBio AG, 2000. (Month Unknown).
Sorting Single Molecules: Application to Diagnostics and Evolutionary Biotechnology, Eigen et al., *PNAS*, vol. 91, pp. 5740–5747, 1994, Jun. 1994.
A Microfabricated Fluorescence–Activated Cell Sorter, Fu et al., *Nature Biotechnology*, vol. 17, pp. 1109–1111, Nov. 1999.

* cited by examiner $\tau_F \ll \tau_{rot}$   $\tau_F \gg \tau_{rot}$

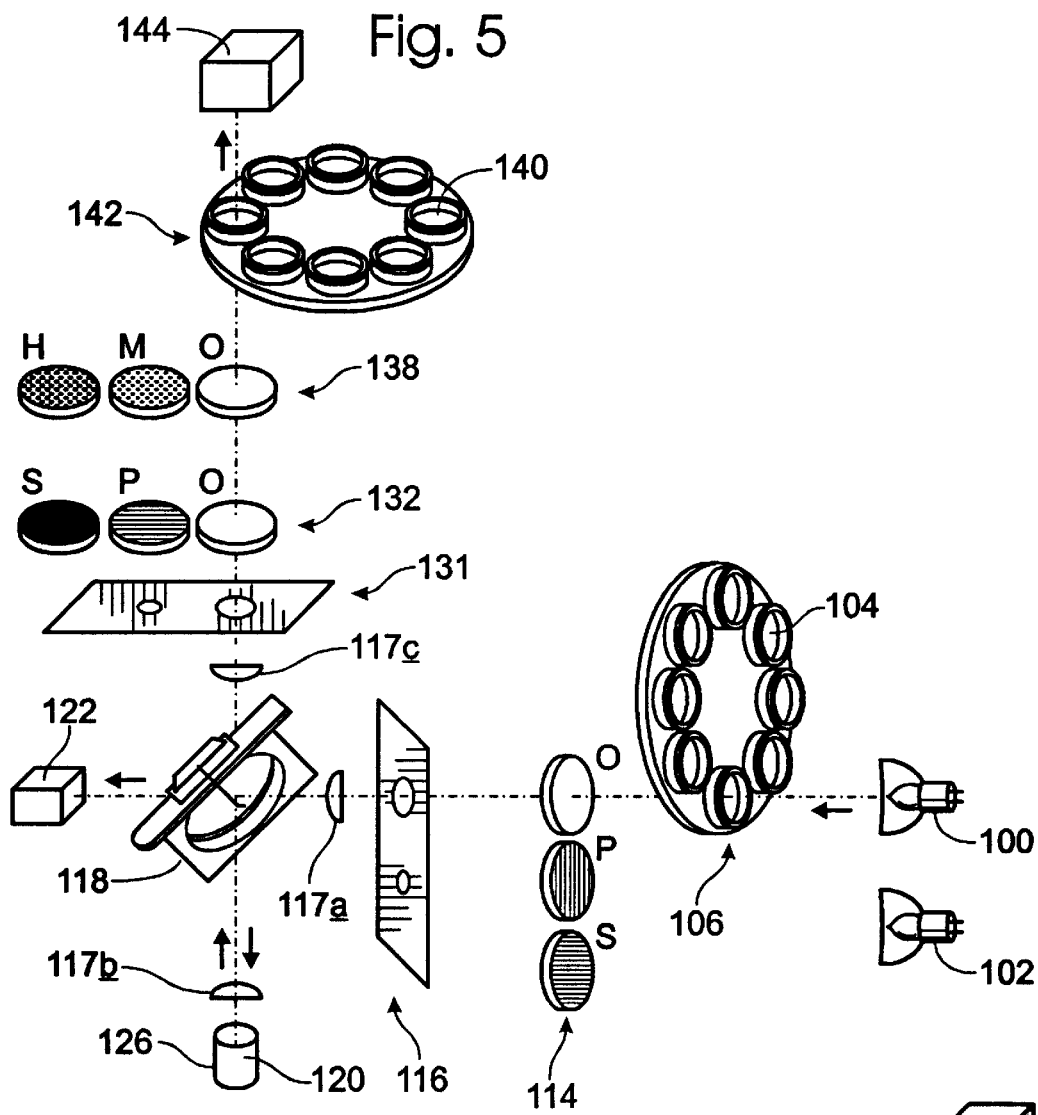
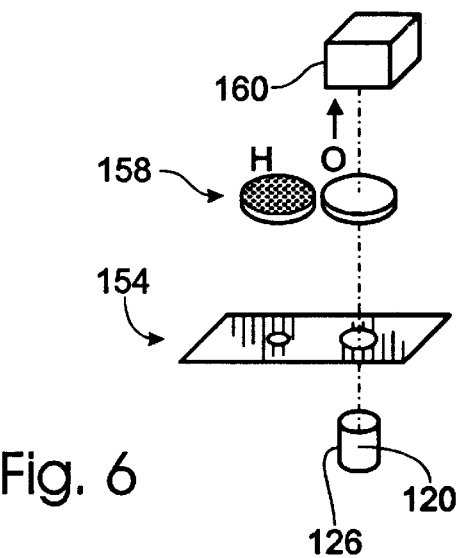

BROAD RANGE LIGHT DETECTION SYSTEM

CROSS-REFERENCES TO RELATED APPLICATIONS

This application is a continuation of PCT patent application Ser. No. PCT/US99/03678, filed Feb. 19, 1999, which is incorporated herein by reference.

This application is a continuation of and claims priority from the following patent applications, each of which is incorporated herein by reference: U.S. patent application Ser. No. 09/062,472, filed Apr. 17, 1998, now issued as U.S. Patent No. 6,071,748, on Jun. 6, 2000; U.S. patent application Ser. No. 09/160,533, filed Sep. 24, 1998, now issued as U.S. Patent No. 6,097,025, on Aug. 1, 2000; PCT application Ser. No. PCT/US98/23095, filed Oct. 30, 1998; and PCT application Ser. No. PCT/US99/01656, filed Jan. 25, 1999.

This application is based upon and claims benefit under 35 U.S.C. § 119 of the following U.S. Provisional Patent Applications, each of which is incorporated herein by reference: Ser. No. 60/075,414, filed Feb. 20, 1998; Ser. No. 60/082,253, filed Apr. 17, 1998; and Ser. No. 60/100,951, filed Sep. 18, 1998.

This application incorporates by reference the following publications: PAUL HOROWITZ & WINFIELD HILL, THE ART OF ELECTRONICS (1980); and JOSEPH R. LAKOWICZ, PRINCIPLES OF FLUORESCENCE SPECTROSCOPY (1983).

FIELD OF THE INVENTION

The invention relates to light detection, and more particularly to a broad-range light-detection system.

BACKGROUND OF THE INVENTION

Systems that involve the detection of light are used in a variety of contexts. In particular, systems that involve the detection and subsequent analysis of light are used in performing optical spectroscopic assays, including luminescence and absorption assays. These assays are used to characterize the components and properties of molecular systems, and recently have been used in high-throughput screening procedures to identify candidate drug compounds. Optical spectroscopic assays include fluorescence polarization (FP), fluorescence resonance energy transfer (FRET), fluorescence lifetime (FLT), total internal reflection (TIR) fluorescence, fluorescence correlation spectroscopy (FCS), and fluorescence recovery after photobleaching (FRAP), and their phosphorescence analogs, among others. Optical spectroscopic assays also include absorption assays.

Unfortunately, light detection systems suffer from a number of shortcomings. Such systems may be limited in range, so that they accurately detect light only within some relatively narrow range of intensities. Such systems also may require user intervention to alter the detection range, if the range may be altered at all. Such systems also may be limited to either discrete or analog detection, so that either they discretely count individual quanta or photons of light, or they integrate an analog value corresponding to such quanta, but they do not do both. Such systems also may require significant periods of time to make measurements. These shortcomings may be found singly or in combination, and these shortcomings may be particularly significant in the context of high-throughput screening, where it may be necessary to perform tens or hundreds of thousands of measurements per day.

SUMMARY OF THE INVENTION

The invention comprises a broad-range light-detection system. In some embodiments, the system includes apparatus and methods for detecting light with high accuracy over a broad range of intensities. In other embodiments, the system includes apparatus and methods for automatically scaling the detection range to improve detection based on the intensity of the detected light. In yet other embodiments, the system includes apparatus and methods for detecting light with increased speed, particularly in applications involving analysis of successive samples.

BRIEF DESCRIPTION OF THE DRAWINGS

FIG. 5 is a schematic view of photoluminescence optical components from the apparatus of FIG. 3.

FIG. 6 is a schematic view of chemiluminescence optical components from the apparatus of FIG. 3.

DETAILED DESCRIPTION OF THE INVENTION

The invention provides apparatus and methods for detecting light, as described below. For clarity, the description is divided into three parts: (1) overview of luminescence assays, (2) description of luminescence apparatus, and (3) detection methods.

1. Overview of Luminescence Assays

Luminescence assays use luminescence emissions from luminescent analytes to study the properties and environment of the analyte, as well as binding reactions and enzymatic activities involving the analyte, among others. In this sense, the analyte may act as a reporter to provide information about another material or target substance that may be the focus of the assay. Luminescence assays may use various aspects of the luminescence, including its intensity, polarization, and lifetime, among others. Luminescence assays also may use time-independent (steady-state) and/or time-dependent (time-resolved) properties of the luminescence. Steady-state assays generally are less complicated than time-resolved assays, but generally yield less information.

Intensity Assays. Luminescence intensity assays involve monitoring the intensity (or amount) of light emitted from a composition. The intensity of emitted light will depend on the extinction coefficient, quantum yield, and number of the luminescent analytes in the composition, among others. These quantities, in turn, will depend on the environment on the analyte, among others, including the proximity and efficacy of quenchers and energy transfer partners. Thus, luminescence intensity assays may be used to study binding reactions, among other applications.

Polarization Assays. Luminescence polarization assays involve the absorption and emission of polarized light, and typically are used to study molecular rotation. (Polarization describes the direction of light's electric field, which generally is perpendicular to the direction of light's propagation.)

Figure 1:
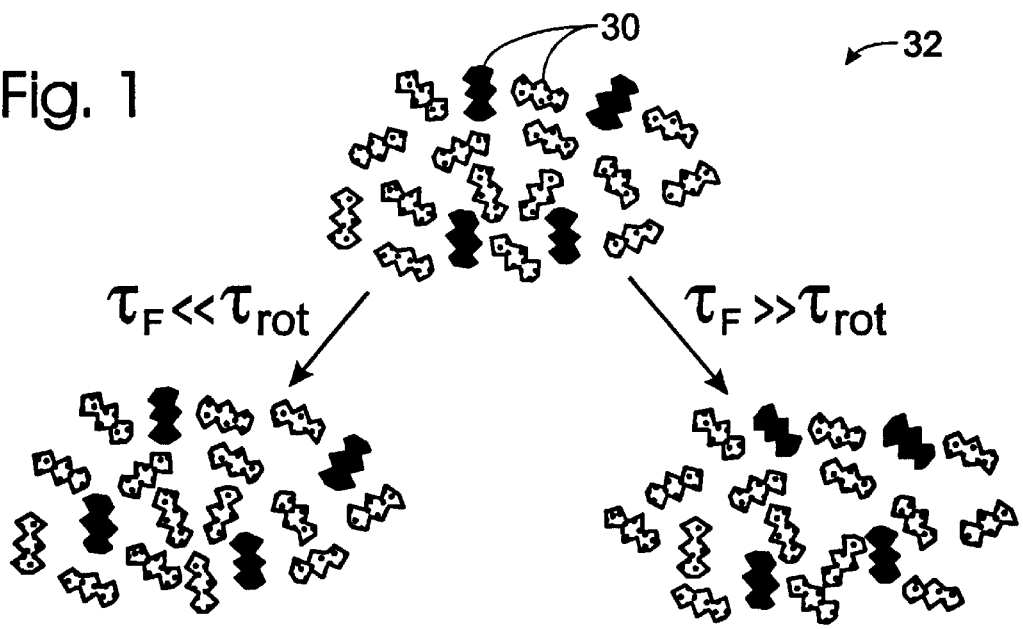
FIG. 1 is a schematic view of fluorescently labeled molecules, showing how molecular reorientation affects fluorescence polarization.

FIG. 1 is a schematic view showing how luminescence polarization is affected by molecular rotation. In a luminescence polarization assay, specific molecules 30 within a composition 32 are labeled with one or more luminophores. The composition then is illuminated with polarized excitation light, which preferentially excites luminophores having absorption dipoles aligned parallel to the polarization of the excitation light. These molecules subsequently decay by preferentially emitting light polarized parallel to their emission dipoles. The extent to which the total emitted light is polarized depends on the extent of molecular reorientation during the time interval between luminescence excitation and emission, which is termed the luminescence lifetime, $\tau$. The extent of molecular reorientation in turn depends on the luminescence lifetime and the size, shape, and environment of the reorienting molecule. Thus, luminescence polarization assays may be used to quantify binding reactions and enzymatic activity, among other applications. In particular, molecules rotate via diffusion with a rotational correlation time $\tau_{rot}$ that is proportional to their size. Thus, during their luminescence lifetime, relatively large molecules will not reorient significantly, so that their total luminescence will be relatively polarized. In contrast, during the same time interval, relatively small molecules will reorient significantly, so that their total luminescence will be relatively unpolarized.

The relationship between polarization and intensity is expressed by the following equation:

$$P = \frac{I_\| - I_\perp}{I_\| + I_\perp} \tag{1}$$

Here, P is the polarization, $I_\|$ is the intensity of luminescence polarized parallel to the polarization of the excitation light, and $I_\perp$ is the intensity of luminescence polarized perpendicular to the polarization of the excitation light. If there is little rotation between excitation and emission, $I_\|$ will be relatively large, $I_\perp$ will be relatively small, and P will be close to one. (P may be less than one even if there is no rotation; for example, P will be less than one if the absorption and emission dipoles are not parallel.) In contrast, if there is significant rotation between absorption and emission, $I_\|$ will be comparable to $I_\perp$, and P will be close to zero. Polarization often is reported in milli-P units (1000×P), which will range between 0 and 1000, because P will range between zero and one.

Polarization also may be described using other equivalent quantities, such as anisotropy. The relationship between anisotropy and intensity is expressed by the following equation:

$$r = \frac{I_\| - I_\perp}{I_\| + 2I_\perp} \tag{2}$$

Here, r is the anisotropy. Polarization and anisotropy include the same information, although anisotropy may be more simply expressed for systems containing more than one luminophore. In the description and claims that follow, these terms may be used interchangeably, and a generic reference to one should be understood to imply a generic reference to the other.

The relationship between polarization and rotation is expressed by the Perrin equation:

$$\left(\frac{1}{P} - \frac{1}{3}\right) = \left(\frac{1}{P_0} - \frac{1}{3}\right) \cdot \left(1 + \frac{\tau}{\tau_{rot}}\right) \tag{3}$$

Here, $P_0$ is the polarization in the absence of molecular motion (intrinsic polarization), $\tau$ is the luminescence lifetime (inverse decay rate) as described above, and $\tau_{rot}$ is the rotational correlation time (inverse rotational rate) as described above.

The Perrin equation shows that luminescence polarization assays are most sensitive when the luminescence lifetime and the rotational correlation time are similar. Rotational correlation time is proportional to molecular weight, increasing by about 1 nanosecond for each 2,400 dalton increase in molecular weight (for a spherical molecule). For shorter lifetime luminophores, such as fluorescein, which has a luminescence lifetime of roughly 4 nanoseconds, luminescence polarization assays are most sensitive for molecular weights less than about 40,000 daltons. For longer lifetime probes, such as Ru(bpy)$_2$dcbpy (ruthenium 2,2'-dibipyridyl 4,4'-dicarboxyl-2,2'-bipyridine), which has a lifetime of roughly 400 nanoseconds, luminescence polarization assays are most sensitive for molecular weights between about 70,000 daltons and 4,000,000 daltons.

Time-Resolved Assays. Time-resolved assays involve measuring the time course of luminescence emission. Time-resolved assays may be conducted in the time domain or in the frequency domain, both of which are functionally equivalent. In a time-domain measurement, the time course of luminescence is monitored directly. Typically, a composition containing a luminescent analyte is illuminated using a narrow pulse of light, and the time dependence of the intensity of the resulting luminescence emission is observed, although other protocols also may be used. For a simple molecule, the luminescence commonly follows a single-exponential decay.

In a frequency-domain measurement, the time course of luminescence is monitored indirectly, in frequency space. Typically, the composition is illuminated using light whose intensity is modulated sinusoidally at a single modulation frequency $f$, although other protocols (such as transforming time-domain data into the frequency domain) also may be used. The intensity of the resulting luminescence emission is modulated at the same frequency as the excitation light. However, the emission will lag the excitation by a phase angle (phase) φ, and the intensity of the emission will be demodulated relative to the intensity of the excitation by a demodulation factor (modulation) M.

Figure 2:
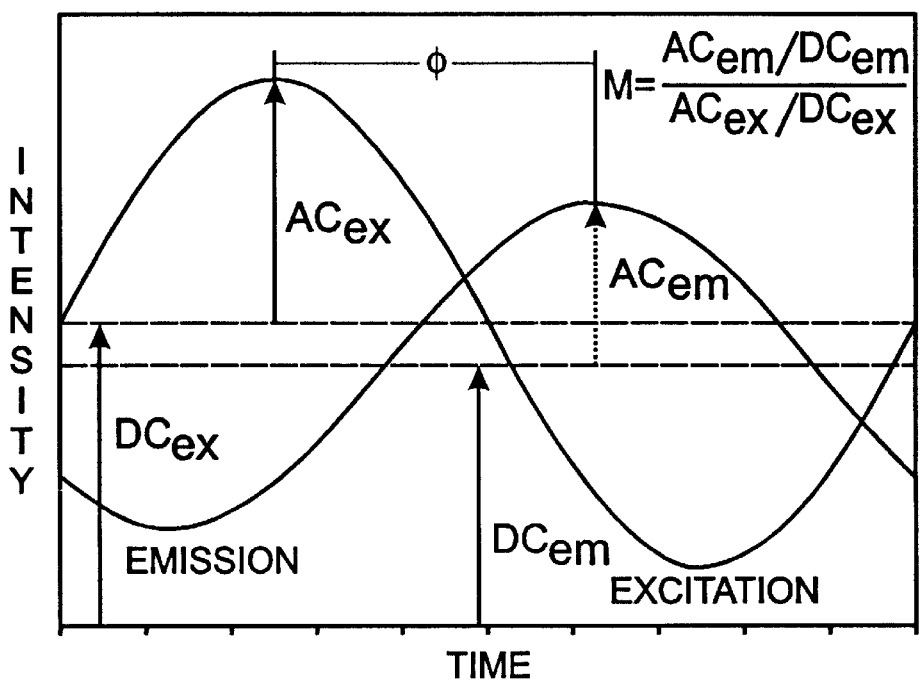
FIG. 2 is a schematic view of a frequency-domain time-resolved measurement, showing the definitions of phase angle (phase) φ and demodulation factor (modulation) M.

FIG. 2 shows the relationship between emission and excitation in a single-frequency frequency-domain experiment. The phase φ is the phase difference between the excitation and emission. The modulation M is the ratio of the AC amplitude to the DC amplitude for the emission, relative to the ratio of the AC amplitude to the DC amplitude for the excitation. The phase and modulation are related to the luminescence lifetime τ by Equations 4 and 5.

$$\omega\tau = \tan(\phi) \quad (4)$$

$$\omega\tau = \sqrt{\frac{1}{M^2} - 1} \quad (5)$$

Here ω is the angular modulation frequency, which equals 2π times the modulation frequency. For maximum sensitivity, the angular modulation frequency should be roughly the inverse of the luminescence lifetime. Lifetimes of interest in high-throughput screening vary from less than 1 nanosecond to greater than 10 microseconds. Therefore, instruments for high-throughput screening should be able to cover modulation frequencies from 20 kHz to 200 MHz.

2. Description of Luminescence Apparatus

FIGS. 3–6 show an apparatus 90 for detecting light emitted by an analyte in a composition. Apparatus 90 includes (1) a stage for supporting the composition, (2) one or more light sources for delivering light to a composition, (3) one or more detectors for receiving light transmitted from the composition and converting it to a signal, (4) first and second optical relay structures for relaying light between the light source, composition, and detector, and (5) a processor for analyzing the signal from the detector. Generally, only a subset of these components are used by the invention.

Apparatus 90 may be used for a variety of assays, including but not limited to the assays described above. These assays generally involve detection of luminescence, which is the emission of light from excited electronic states of atoms or molecules. Luminescence generally refers to all kinds of light emission, except incandescence, and may include photoluminescence, chemiluminescence, and electrochemiluminescence, among others. In photoluminescence, including fluorescence and phosphorescence, the excited electronic state is created by the absorption of electromagnetic radiation. In chemiluminescence, which includes bioluminescence, the excited electronic state is created by a transfer of chemical energy. In electrochemiluminescence, the excited electronic state is created by an electrochemical process.

Components of the optical system are chosen to optimize sensitivity and dynamic range for each assay supported by the analyzer. Toward this end, optical components with low intrinsic luminescence are chosen. In addition, some components are shared by different modes, whereas other components are unique to a particular mode. For example, photoluminescence intensity and steady-state photoluminescence polarization modes share a light source; time-resolved luminescence modes use their own light source; and chemiluminescence modes do not use a light source. Similarly, photoluminescence and chemiluminescence modes use different detectors.

The remainder of this section is divided into five subsections: (1) photoluminescence optical system, (2) chemiluminescence optical system, (3) housing, (4) alternative apparatus, and (5) methods.

Photoluminescence optical system. As configured here, apparatus 90 includes a continuous light source 100 and a time-modulated light source 102. Apparatus 90 includes light source slots 103a–d for four light sources, although other numbers of light source slots and light sources also could be provided. Light source slots 103a–d function as housings that may surround at least a portion of each light source, providing some protection from radiation and explosion. The direction of light transmission through the photoluminescence optical system is indicated by arrows.

Continuous source 100 provides light for photoluminescence intensity and steady-state photoluminescence polarization assays. Continuous light source 100 may include arc lamps, lasers, laser diodes, and light-emitting diodes (LEDs), among others. A preferred continuous source is a high-intensity, high color temperature xenon arc lamp, such as a Model LX175F CERMAX xenon lamp from ILC Technology, Inc. Color temperature is the absolute temperature in Kelvin at which a blackbody radiator must be operated to have a chromaticity equal to that of the light source. A high color temperature lamp produces more light than a low color temperature lamp, and it may have a maximum output shifted toward or into visible wavelengths and ultraviolet wavelengths where many luminophores absorb. The preferred continuous source has a color temperature of 5600 Kelvin, greatly exceeding the color temperature of about 3000 Kelvin for a tungsten filament source. The preferred source provides more light per unit time than flash sources, increasing sensitivity and reducing read times. Apparatus 90 may include a modulator mechanism configured to vary the intensity of light incident on the composition without varying the intensity of light produced by the light source.

Time-modulated source 102 provides light for time-resolved photoluminescence assays, such as photoluminescence lifetime and time-resolved photoluminescence polarization assays. A preferred time-modulated source is a xenon flash lamp, such as a Model FX-1160 xenon flash lamp from EG&G Electro-Optics. The preferred source produces a "flash" of light for a brief interval before signal detection and is especially well suited for time-domain measurements. Other time-modulated sources include pulsed lasers, as well as continuous lamps whose intensity can be modulated extrinsically using a Pockels cell, Kerr cell, or other mechanism. The latter sources are especially well suited for frequency-domain measurements.

In apparatus 90, continuous source 100 and time-modulated source 102 produce multichromatic, unpolarized, and incoherent light. Continuous source 100 produces substantially continuous illumination, whereas time-modulated source 102 produces time-modulated illumination. Light from these light sources may be delivered to the sample without modification, or it may be filtered to alter its intensity, spectrum, polarization, or other properties.

Light produced by the light sources follows an excitation optical path to an examination site. Such light may pass through one or more "spectral filters," which generally comprise any mechanism for altering the spectrum of light that is delivered to the sample. Spectrum refers to the wavelength composition of light. A spectral filter may be used to convert white or multichromatic light, which includes light of many colors, into red, blue, green, or other substantially monochromatic light, which includes light of one or only a few colors. In apparatus 90, spectrum is altered by an excitation interference filter 104, which selectively transmits light of preselected wavelengths and selectively absorbs light of other wavelengths. For convenience, excitation interference filters 104 may be housed in an excitation filter wheel 106, which allows the spectrum of excitation light to be changed by rotating a preselected filter into the optical path. Spectral filters also may separate light spatially by wavelength. Examples include gratings, monochromators, and prisms.

Spectral filters are not required for monochromatic ("single color") light sources, such as certain lasers, which output light of only a single wavelength. Therefore, excitation filter wheel 106 may be mounted in the optical path of some light source slots 103*a,b*, but not other light source slots 103*c,d*.

Light next passes through an excitation optical shuttle (or switch) 108, which positions an excitation fiber optic cable 110*a,b* in front of the appropriate light source to deliver light to top or bottom optics heads 112*a,b*, respectively. The optics heads include various optics for delivering light into the sensed volume and for receiving light transmitted from the sensed volume. Light is transmitted through a fiber optic cable much like water is transmitted through a garden hose. Fiber optic cables can be used easily to turn light around corners and to route light around opaque components of the apparatus. Moreover, fiber optic cables give the light a more uniform intensity profile. A preferred fiber optic cable is a fused silicon bundle, which has low autoluminescence. Despite these advantages, light also can be delivered to the optics heads using other mechanisms, such as mirrors.

Light arriving at the optics head may pass through one or more excitation "polarization filters," which generally comprise any mechanism for altering the polarization of light. Excitation polarization filters may be included with the top and/or bottom optics head. In apparatus 90, polarization is altered by excitation polarizers 114, which are included only with top optics head 112*a*. Excitation polarization filters 114 may include an s-polarizer S that passes only s-polarized light, a p-polarizer P that passes only p-polarized light, and a blank O that passes substantially all light. Excitation polarizers 114 also may include a standard or ferro-electric liquid crystal display (LCD) polarization switching system. Such a system is faster and more economical than a mechanical switcher. Excitation polarizers 114 also may include a continuous mode LCD polarization rotator with synchronous detection to increase the signal-to-noise ratio in polarization assays. Excitation polarizers 114 may be included in light sources, such as certain lasers, that intrinsically produce polarized light.

Light at one or both optics heads also may pass through an excitation "confocal optics element," which generally comprises any mechanism for focusing light into a "sensed volume." In apparatus 90, the confocal optics element includes a set of lenses 117*a–c* and an excitation aperture 116 placed in an image plane conjugate to the sensed volume, as shown in FIG. 5. Aperture 116 may be implemented directly, as an aperture, or indirectly, as the end of a fiber optic cable. Lenses 117*a,b* project an image of aperture 116 onto the sample, so that only a preselected or sensed volume of the sample is illuminated.

Light traveling through the optics heads is reflected and transmitted through a beamsplitter 118, which delivers reflected light to a composition 120 and transmitted light to a light monitor 122. Reflected and transmitted light both pass through lens 117*b*, which is operatively positioned between beamsplitter 118 and composition 120, Beamsplitter 118 is used to direct excitation light toward the sample and light monitor, and to direct emission light toward the detector. The beamsplitter is changeable, so that it may be optimized for different assay modes or compositions. If a large number or variety of luminescent molecules are to be studied, the beamsplitter must be able to accommodate light of many wavelengths; in this case, a "50:50" beamsplitter that reflects half and transmits half of the incident light independent of wavelength is optimal. Such a beamsplitter can be used with many types of molecules, while still delivering considerable excitation light onto the composition, and while still transmitting considerable emission light to the detector. If one or a few related luminescent molecules are to be studied, the beamsplitter needs only to be able to accommodate light at a limited number of wavelengths; in this case, a "dichroic" or "multichroic" beamsplitter is optimal. Such a beamsplitter can be designed with cutoff wavelengths for the appropriate set of molecules and will reflect most or substantially all of the excitation and background light, while transmitting most or substantially all of the emission light. This is possible because the reflectivity and transmissivity of the beamsplitter can be varied with wavelength.

Light monitor 122 is used to correct for fluctuations in the intensity of light provided by the light sources; such corrections may be performed by reporting detected intensities as a ratio over corresponding times of the luminescence intensity measured by the detector to the excitation light intensity measured by the light monitor. The light monitor also can be programmed to alert the user if the light source fails. A preferred light monitor is a silicon photodiode with a quartz window for low autoluminescence.

The composition (or sample) may be held in a sample holder supported by a stage 123. The composition can include compounds, mixtures, surfaces, solutions, emulsions, suspensions, cell cultures, fermentation cultures, cells, tissues, secretions, and/or derivatives and/or extracts thereof Analysis of the composition may involve measuring the presence, concentration, or physical properties (including interactions) of a photoluminescent analyte in such a composition. The sample holder can include microplates, biochips, or any array of samples in a known format. In apparatus 90, the preferred sample holder is a microplate 124, which includes a plurality of microplate wells 126 for holding compositions. Composition may refer to the contents of a single microplate well, or several microplate wells, depending on the assay. In some embodiments, such as a portable analyzer, the stage may be intrinsic to the instrument.

The sensed volume typically has an hourglass shape, with a cone angle of about 25° and a minimum diameter ranging between 0.1 mm and 2.0 mm. For 96-well and 384-well microplates, a preferred minimum diameter is about 1.5 mm. For 1536-well microplates, a preferred minimum diameter is about 1.0 mm. The size and shape of the sample container may be matched to the size and shape of the sensed volume.

Figure 3:
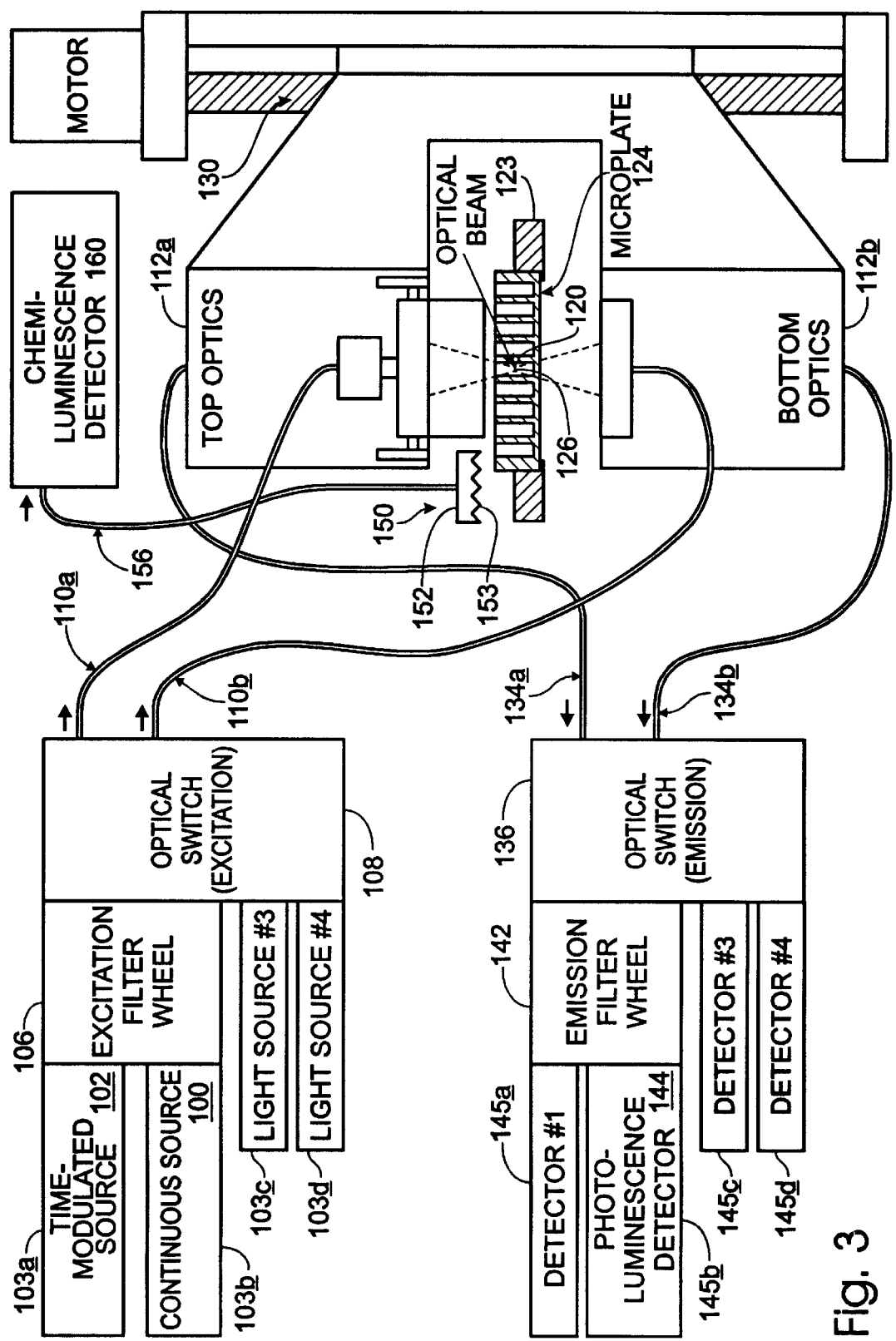
FIG. 3 is a schematic view of an apparatus for detecting light in accordance with the invention.
Figure 4:
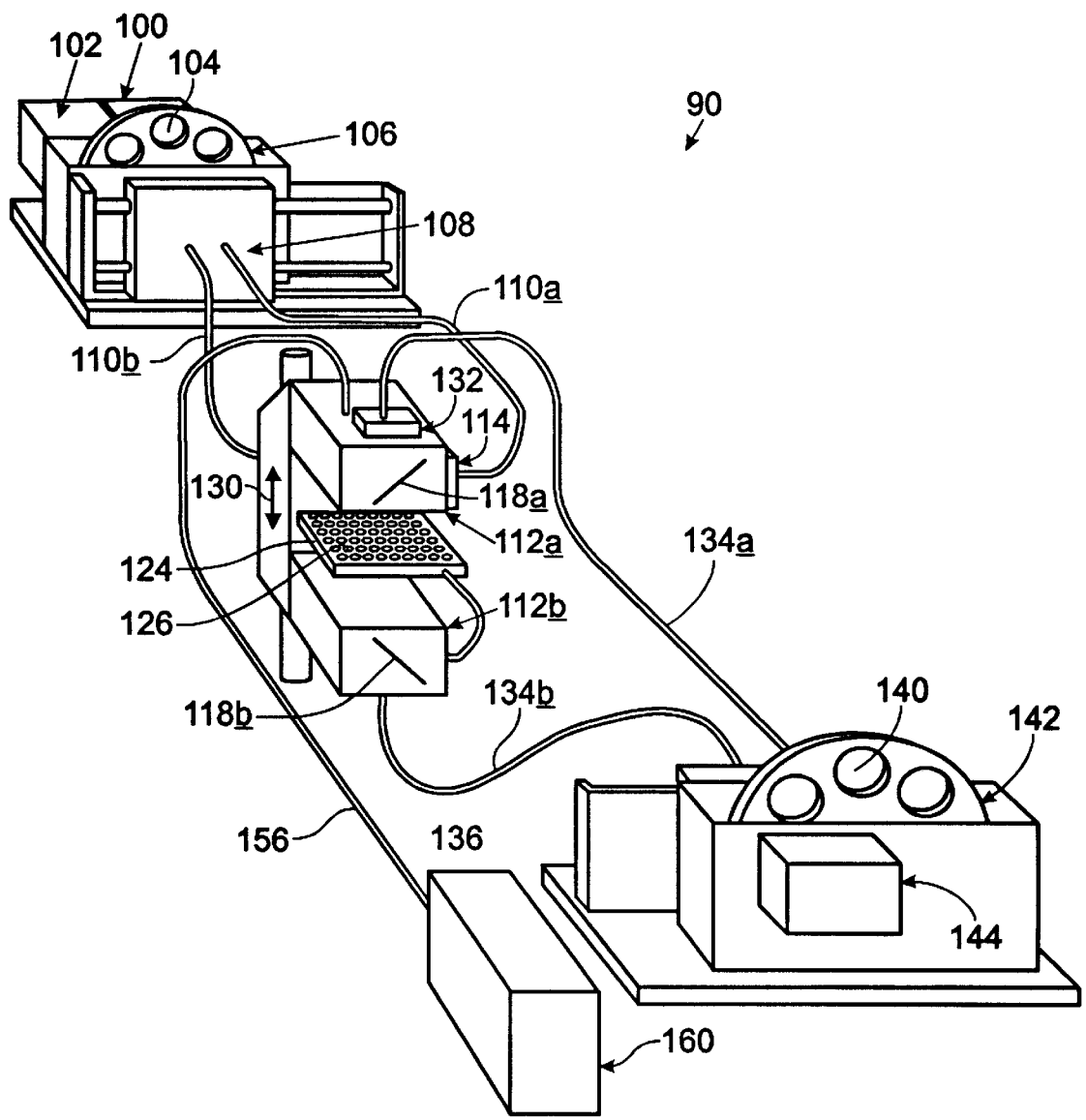
FIG. 4 is a partially schematic perspective view of the apparatus of FIG. 3.

The position of the sensed volume can be moved precisely within the composition to optimize the signal-to-noise and signal-to-background ratios. For example, the sensed volume may be moved away from walls in the sample holder to optimize signal-to-noise and signal-to-background ratios, reducing spurious signals that might arise from luminophores bound to the walls and thereby immobilized. In apparatus 90, position in the X,Y-plane perpendicular to the optical path is controlled by moving the stage supporting the composition, whereas position along the Z-axis parallel to the optical path is controlled by moving the optics heads using a Z-axis adjustment mechanism 130, as shown in FIGS. 3 and 4. However, any mechanism for bringing the sensed volume into register or alignment with the appropriate portion of the composition also may be employed.

The combination of top and bottom optics permits assays to combine: (1) top illumination and top detection, or (2) top illumination and bottom detection, or (3) bottom illumination and top detection, or (4) bottom illumination and bottom detection. Same-side illumination and detection (1) and (4) is referred to as "epi" and is preferred for photoluminescence assays. Opposite-side illumination and detection (2) and (3) is referred to as "trans" and is preferred for absorbance assays. In apparatus 90, epi modes are supported, so the excitation and emission light travel the same path in the optics head, albeit in opposite or anti-parallel directions. However, trans modes also could be supported and would be essential for absorbance assays. Generally, top optics can be used with any sample holder having an open top, whereas bottom optics can be used only with sample holders having optically transparent bottoms, such as glass or thin plastic bottoms.

Light is transmitted by the composition in multiple directions. A portion of the transmitted light will follow an emission pathway to a detector. Transmitted light passes through lens 117c and may pass through an emission aperture 131 and/or an emission polarizer 132. In apparatus 90, the emission aperture is placed in an image plane conjugate to the sensed volume and transmits light substantially exclusively from this sensed volume. In apparatus 90, the emission apertures in the top and bottom optical systems are the same size as the associated excitation apertures, although other sizes also may be used. The emission polarizers are included only with top optics head 112a. The emission aperture and emission polarizer are substantially similar to their excitation counterparts. Emission polarizer 132 may be included in detectors that intrinsically detect the polarization of light.

Excitation polarizers 114 and emission polarizers 132 may be used together in nonpolarization assays to reject certain background signals. Luminescence from the sample holder and from luminescent molecules adhered to the sample holder is expected to be polarized, because the rotational mobility of these molecules should be hindered. Such polarized background signals can be eliminated by "crossing" the excitation and emission polarizers, that is, setting the angle between their transmission axes at 90°. As described above, such polarized background signals also can be reduced by moving the sensed volume away from walls of the sample holder. To increase signal level, beamsplitter 118 should be optimized for reflection of one polarization and transmission of the other polarization. This method will work best where the luminescent molecules of interest emit relatively unpolarized light, as will be true for small luminescent molecules in solution.

Transmitted light next passes through an emission fiber optic cable 134a,b to an emission optical shuttle (or switch) 136. This shuttle positions the appropriate emission fiber optic cable in front of the appropriate detector. In apparatus 90, these components are substantially similar to their excitation counterparts, although other mechanisms also could be employed.

Light exiting the fiber optic cable next may pass through one or more emission "intensity filters," which generally comprise any mechanism for reducing the intensity of light. Intensity refers to the amount of light per unit area per unit time. In apparatus 90, intensity is altered by emission neutral density filters 138, which absorb light substantially independent of its wavelength, dissipating the absorbed energy as heat. Emission neutral density filters 138 may include a high-density filter H that absorbs most incident light, a medium-density filter M that absorbs somewhat less incident light, and a blank O that absorbs substantially no incident light. These filters are changed by hand, although other methods also could be employed, such as a filter wheel. Intensity filters also may divert a portion of the light away from the sample without absorption. Examples include beam splitters, which transmit some light along one path and reflect other light along another path, and Pockels cells, which deflect light along different paths through diffraction.

Light next may pass through an emission interference filter 140, which may be housed in an emission filter wheel 142. In apparatus 90, these components are substantially similar to their excitation counterparts, although other mechanisms also could be employed. Emission interference filters block stray excitation light, which may enter the emission path through various mechanisms, including reflection and scattering. If unblocked, such stray excitation light could be detected and misidentified as photoluminescence, decreasing the signal-to-background ratio. Emission interference filters can separate photoluminescence from excitation light because photoluminescence has longer wavelengths than the associated excitation light. Luminescence typically has wavelengths between 200 and 2000 nanometers.

The relative positions of the spectral, intensity, polarization, and other filters presented in this description may be varied without departing from the spirit of the invention. For example, filters used here in only one optical path, such as intensity filters, also may be used in other optical paths. In addition, filters used here in only top or bottom optics, such as polarization filters, may also be used in the other of top or bottom optics or in both top and bottom optics. The optimal positions and combinations of filters for a particular experiment will depend on the assay mode and the composition, among other factors.

Light last passes to a detector, which is used in absorbance and photoluminescence assays. In apparatus 90, there is one photoluminescence detector 144, which detects light from all photoluminescence modes. A preferred detector is a photomultiplier tube (PMT). Apparatus 90 includes detector slots 145a–d for four detectors, although other numbers of detector slots and detectors also could be provided.

More generally, detectors comprise any mechanism capable of converting energy from detected light into signals that may be processed by the apparatus, and by the processor in particular. Suitable detectors include photomultiplier tubes, photodiodes, avalanche photodiodes, charge-coupled devices (CCDs), and intensified CCDs, among others. Depending on the detector, light source, and assay mode, such detectors may be used in a variety of detection modes. These detection modes include (1) discrete (e.g., photon-counting) modes, (2) analog (e.g., culent-integration) modes, and/or (3) imaging modes, among others, as described below.

Chemiluminescence optical system. FIGS. 3, 4, and 6 show the chemiluminescence optical system of analyzer 50. Because chemiluminescence follows a chemical event rather than the absorption of light, the chemiluminescence optical system does not require a light source or other excitation optical components. Instead, the chemiluminescence optical system requires only selected emission optical components. In analyzer 50, a separate lensless chemiluminescence optical system is employed, which is optimized for maximum sensitivity in the detection of chemiluminescence.

Generally, components of the chemiluminescence optical system perform the same functions and are subject to the same caveats and alternatives as their counterparts in the photoluminescence optical system. The chemiluminescence optical system also can be used for other assay modes that do not require illumination, such as electrochemiluminescence.

The chemiluminescence optical path begins with a chemiluminescent composition 120 held in a sample container 126. The composition and sample container are analogous to those used in photoluminescence assays; however, analysis of the composition involves measuring the intensity of light generated by a chemiluminescence reaction within the composition rather than by light-induced photoluminescence. A familiar example of chemiluminescence is the glow of the firefly.

Chemiluminescence light typically is transmitted from the composition in all directions, although most will be absorbed or reflected by the walls of the sample container. A portion of the light transmitted through the top of the well is collected using a chemiluminescence head 150, as shown in FIG. 3, and will follow a chemiluminescence optical pathway to a detector. The direction of light transmission through the chemiluminescence optical system is indicated by arrows.

The chemiluminescence head includes a nonconfocal mechanism for transmitting light from a sensed volume within the composition. Detecting from a sensed volume reduces contributions to the chemiluminescence signal resulting from "cross talk," which is pickup from neighboring wells. The nonconfocal mechanism includes a chemiluminescence baffle 152, which includes rugosities 153 that absorb or reflect light from other wells. The nonconfocal mechanism also includes a chemiluminescence aperture 154 that further confines detection to a sensed volume.

Light next passes through a chemiluminescence fiber optic cable 156, which may be replaced by any suitable mechanism for directing light from the composition toward the detector. Fiber optic cable 156 is analogous to excitation and emission fiber optic cables 110a,b and 134a,b in the photoluminescence optical system. Fiber optic cable 156 may include a transparent, open-ended lumen that may be filled with fluid. This lumen would allow the fiber optic to be used both to transmit luminescence from a microplate well and to dispense fluids into the microplate well. The effect of such a lumen on the optical properties of the fiber optic could be minimized by employing transparent fluids having optical indices matched to the optical index of the fiber optic.

Light next passes through one or more chemiluminescence intensity filters, which generally comprise any mechanism for reducing the intensity of light. In analyzer 50, intensity is altered by chemiluminescence neutral density filters 158. Light also may pass through other filters, if desired.

Light last passes to a detector, which converts light into signals that may be processed by the analyzer. In analyzer 50, there is one chemiluminescence detector 160. This detector may be selected to optimize detection of blue/green light, which is the type most often produced in chemiluminescence. A preferred detection is a photomultiplier tube, selected for high quantum efficiency and low dark count at chemiluminescence wavelengths (400–500 nanometers).

Figure 7:
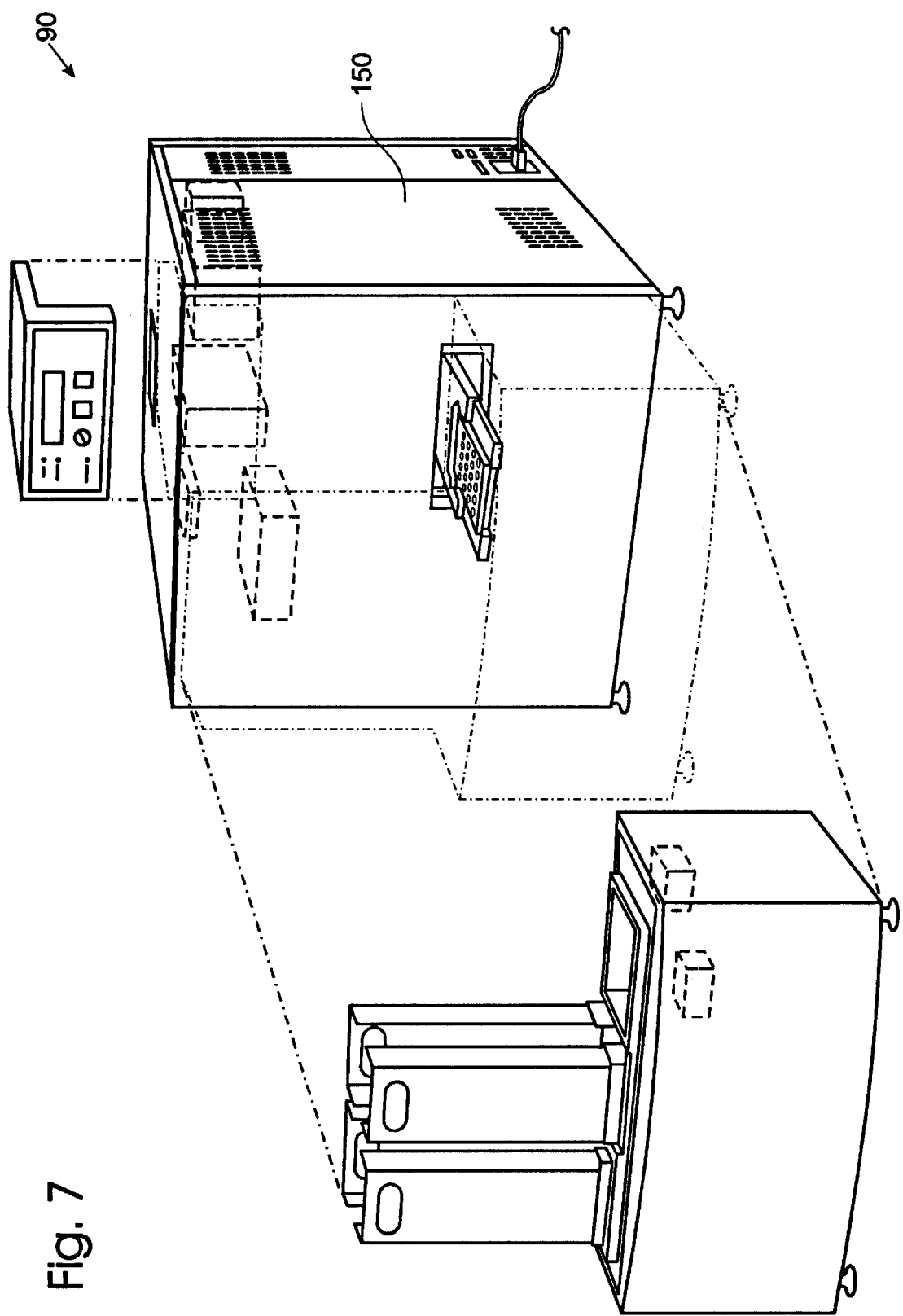
FIG. 7 is a partially exploded perspective view of a housing for the apparatus of FIGS. 1 and 2.

Housing. FIG. 7 shows a housing 150 and other accessories for the apparatus of FIGS. 3–6. Housing 150 substantially encloses the apparatus, forming (together with light source slots 103a–d) two protective layers around the continuous high color temperature xenon arc lamp. Housing 150 permits automated sample loading and switching among light sources and detectors, further protecting the operator from the xenon arc lamp and other components of the system.

Figure 8:
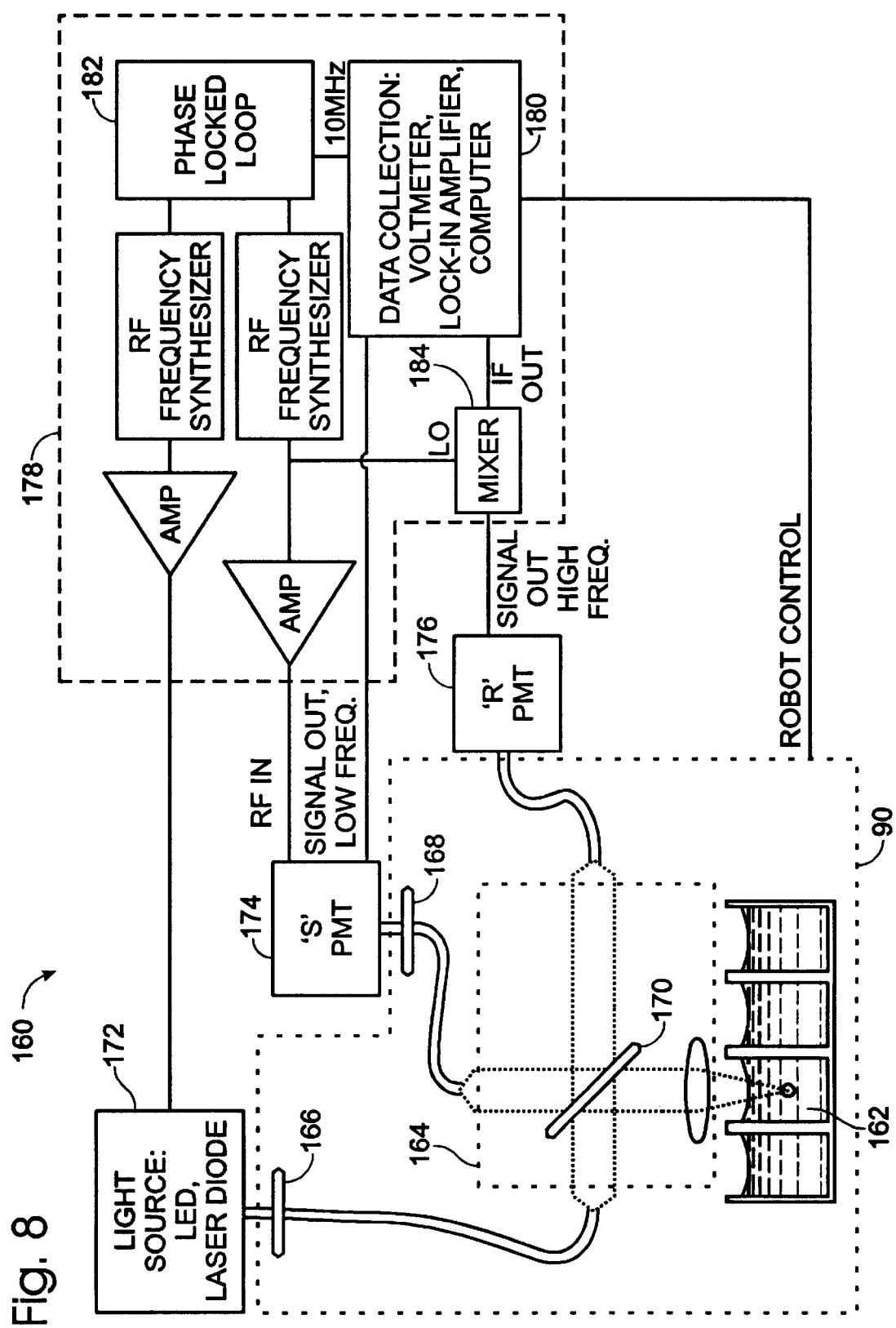
FIG. 8 is a schematic view of an alternative apparatus for detecting light in accordance with the invention.

Alternative apparatus. FIG. 8 shows an alternative apparatus 160 for detecting light emitted by an analyte in a composition 162. Apparatus 160 includes substantial portions of apparatus 90, including its fiber-optic-coupled optics head 164, excitation 166 and emission 168 filters, dichroic beam splitter 170, and mechanisms for sample positioning and focus control. However, apparatus 160 also may include alternative light sources 172, alternative sample ('S') 174 and reference ('R') 176 detectors, and alternative detection electronics 178. In FIG. 8, alternative components 172–178 are shown outside apparatus 90, but they readily may be included inside housing 150 of apparatus 90, if desired.

Apparatus 160 may excite luminescence in various ways, such as using an LED or laser diode light source. For example, analytes absorbing blue light may be excited using a NICHIA-brand bright-blue LED (Model Number NSPB500; Mountville, Pa.). This LED produces broad-spectrum excitation light, so excitation filter 166 typically is used to block the red edge of the spectrum. If analytes are excited using a laser diode, an excitation filter is not necessary.

Apparatus 160 may detect luminescence and convert it to a signal in various ways. Luminescence can be detected using sample PMT 174, which may be an ISS-brand gain-modulated PMT (Champaign, Ill.). High-frequency luminescence can be frequency down-converted to a low-frequency signal using a technique called heterodyning. The phase and modulation of the low-frequency signal can be determined using a lock-in amplifier 180, such as a STANFORD RESEARCH SYSTEMS brand lock-in amplifier (Model Number SR830; Sunnyvale, Calif.). Lock-in amplifier 180 is phase locked using a phase-locked loop 182 to the modulation frequency of light source 172. To correct for drift in the light source, the output of light source 172 may be monitored using reference PMT 176, which may be a HAMAMATSU-brand PMT (Model Number H6780; Bridgewater, N.J.). If reference PMT 176 can respond to high-frequency signals, the heterodyning step can be performed using an external mixer 184. The phase and modulation of reference PMT 176 also may be captured by lock-in amplifier 180 and used to normalize the signal from sample PMT 174.

A computer or processor controls the apparatus, including the external components. The computer also directs sample handling and data collection. Generally, phase and modulation data are collected at one or more frequencies appropriate for the lifetime of the analyte. In some cases, phase and modulation may be measured at one or a few frequencies and processed by the computer or processor to help reduce detected background.

Methods. Apparatus 90 and apparatus 160 both may be used to conduct a variety of steady-state and time-resolved luminescence assays. Steady-state assays measure luminescence under constant illumination, using the continuous light source. Time-resolved polarization assays measure luminescence as a function of time, using either the continuous light source, with its intensity appropriately modulated, or the time-varying light source.

Intensity assays may be conducted by monitoring the intensity of the luminescence emitted by the composition.

Polarization assays may be conducted as follows. Excitation light from the continuous light source is directed through an excitation filter, low-luminescence fiber optic cable, and excitation polarization filter. Excitation light then is directed to a beamsplitter, which reflects most of the light onto a composition and transmits a little of the light into a light monitor. Emitted light from the composition is directed back through the beamsplitter and then is directed through another low-luminescence fiber optic cable, an emission filter, and a polarization filter (in either the S or P orientation) before detection by a photomultiplier tube. Two measurements are performed for each composition, one with excitation and emission polarizers aligned and one with excitation and emission polarizers crossed. Either polarizer may be static or dynamic, and either polarizer may be set in the S or P orientation, although typically the excitation polarizer is set in the S orientation.

Additional luminescence assays, including FRET, FLT, TIR, FCS, and FRAP, as well as their phosphorescence analogs, may be conducted using procedures outlined in PRINCIPLES OF FLUORESCENCE SPECTROSCOPY and generally known to persons of ordinary skill in the art.

3. Detection Modes

Figure 9:
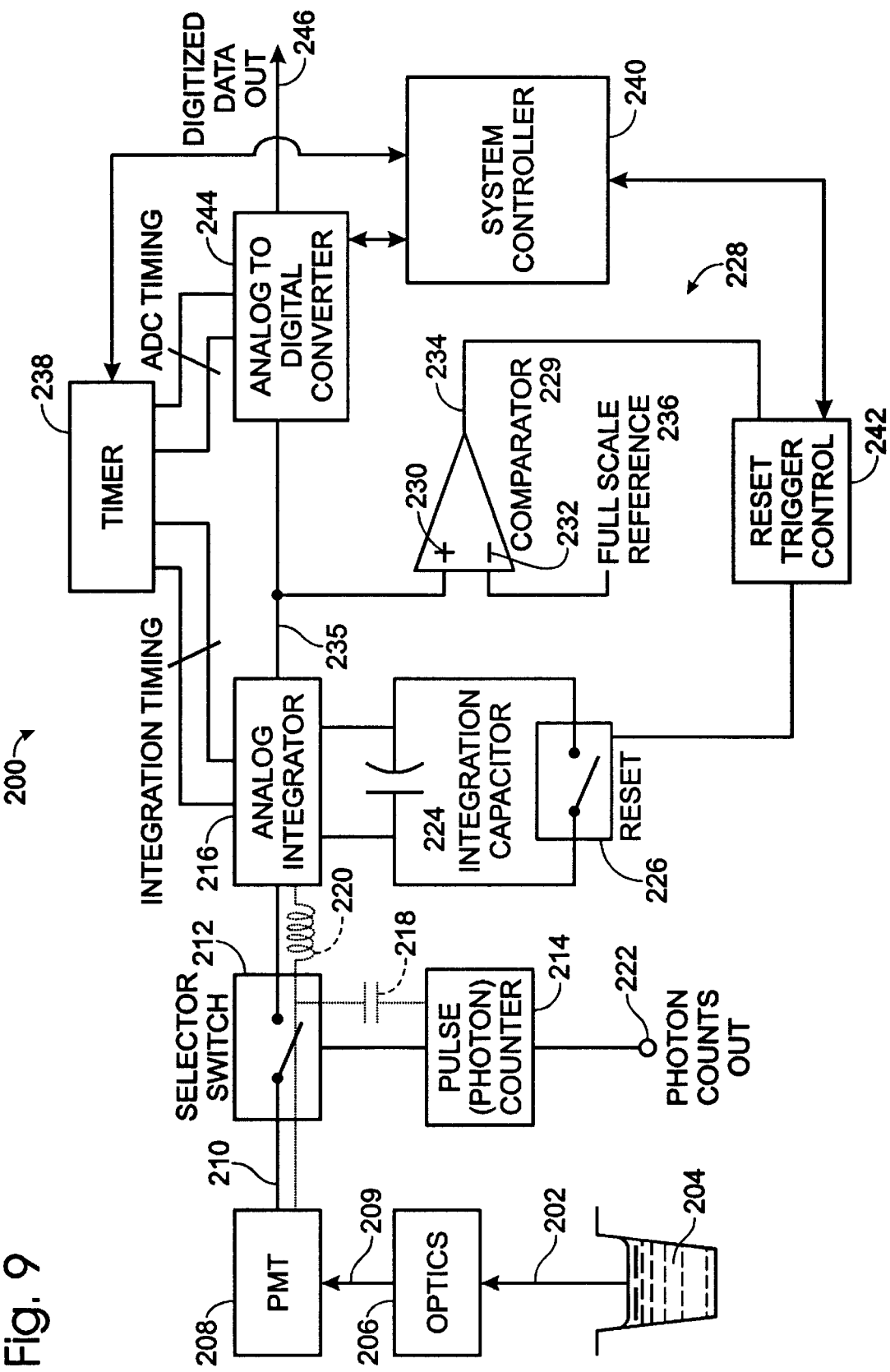
FIG. 9 is a block diagram of a device for detecting light in accordance with the invention.

FIG. 9 is a block diagram showing a device 200 for detecting light in accordance with the invention. In this embodiment, light 202 leaving a composition 204 is directed by appropriate optics 206 to a detector 208. Optics 206 and detector 208 may take various forms, including forms shown in FIGS. 3–8 and described above. Generally, detector 208 has an input 209 that receives light and an output 210 that corresponds to the received light. Output 210 may take various forms, including current and/or voltage signals. Depending on the intensity of the light being received by the detector, the output may be discrete pulses corresponding to individual photons or an analog voltage or current proportional to the incident light.

In device 200, output 210 is directed through a selector switch 212, which selectively routes the output toward various detection components, including a pulse (photon) counter 214 and an analog integrator 216. Selector switch 212 may be manual, permitting a user to select between detection components. Alternatively, selector switch 212 may be passive, allowing use of both detection components based on the intensity of light and/or the type of assay, among others. A passive selector switch may be constructed by omitting switch 212 and connecting a capacitor 218 from the output of the detector to pulse counter 214, and an inductor 220 from the output of the detector to analog integrator 216. Capacitor 218 will pass AC components of output 210 to pulse counter 214, while inductor 220 passes the DC component of output 210 to analog integrator 216. Typical capacitances for capacitor 218 range between 1 and 10 nanoFarads, and typical inductances for inductor 220 range between 0.1 and 1 microHentys. As another alternative, selector switch may be an electronically controlled switching device such as a solid-state switch or a relay, thereby allowing automatic control of the switch to accommodate expected or measured light levels.

Pulse counter 214 is used as a discrete accumulator or integrator to monitor or sample the detected light by counting the number of photons in the detected light. Typically, a detector is chosen that generates an output corresponding to each detected photon. For example, photomultiplier tubes (PMTs) generate a current pulse for each photon that strikes the photocathode in the PMT. The discrete output from the detector may be summed over a sampling period or integration time, and the amount of detected light may be reported in units of counts, counts/second, or relative fluorescence units (RFUs), among others, using an associated output port 222. These results may be corrected for fluctuations in light source intensity if they represent photoluminescence, using a reference detector as described above.

Analog integrator 216 is used as an analog accumulator to monitor the detected light by generating a signal corresponding to the output of the detector. For example, current pulses from a PMT or other detector may be stored (integrated) using a capacitor 224 or other storage component in an electronic circuit. As the capacitor is charged, the analog voltage across the capacitor increases in proportion to the total number of photons collected by the PMT during the integration time. Typical capacitances range between 0.22 and 100 nanoFarads. Typical capacitors include low-leakage polystyrene and polyester capacitors to minimize drift error. Results from the analog integrator most naturally are reported in RFUs; however, the invention also provides for reporting results in terms of counts or counts/second. These results also may be corrected using a reference detector, if appropriate.

The size of capacitor 224 should be selected, manually or automatically, to optimize the precision and range of detection. Generally, the greatest precision is obtained with the smallest capacitor, and the greatest range is obtained with the largest capacitor. Capacitor rating is determined by total counts, not counts/second, because saturation is determined by total counts or its analog counterpart. For a continuous light source, the total number of counts is given by the integral of the counts/second with respect to the integration time. For a flash lamp, the total number of counts is given by the product of the counts per flash and the number of flashes. Generally, the capacitor is zeroed using a reset 226 before each sampling period, and the capacitor is charged to one-half to three-fourths full during each sampling period, with two-thirds full being a preferred value. To maximize flexibility, the apparatus may include a plurality of capacitors or other storage components, each with different capacities. Alternatively, an amplifier or attenuator can be selectively placed between the detector output and integrator input to scale the output of the detector to a range which can be integrated without exceeding the capacity of the storage component for the expected light intensity. The output can be scaled to account for amplification or attenuation caused by the amplifier or attenuator, respectively.

The output signal from the integrator may be fed to a range monitoring device 228, which may include a threshold detection device in the form of operational amplifier or comparator 229. Comparator 229 includes a positive input 230, a negative input 232, and an output 234. Positive input 230 is coupled to the output signal from the integrator. Negative input 232 is connected to a full-scale range reference 236, which typically is a voltage reference. The reference may be adjustable over a range, for example, by using a potentiometer configured as a voltage divider. The reference also may be fixed at a particular value, for example, by using a Zener diode. The output of the comparator is low as long as the voltage at negative input 232 exceeds the voltage at positive input 230. However, when the integrator output signal voltage exceeds reference voltage 236, the output of the comparator will swing to high. Thus, by monitoring the output of the comparator, it is possible to detect if and when the reference value has been exceeded. The output signal of the integrator may be monitored in other ways as well, including digitally or with other analog circuitry.

The timing of detection may be specified and monitored using one or more timers 238 and system controllers 240. Before detecting light from a sample, system controller 240 may zero timer 238, and zero analog integrator 216 using a trigger controller 242 and reset 226. After completing the sample period, system controller 240 may process the integrated signal stored on analog integrator 216 using an analog-to-digital converter 244, and output the data and the sampling time using an associated output port 246. Of course, other mechanisms for preparing the analog integrator for data collection and for outputting data from the analog integrator after data collection also may be employed.

Figure 10:
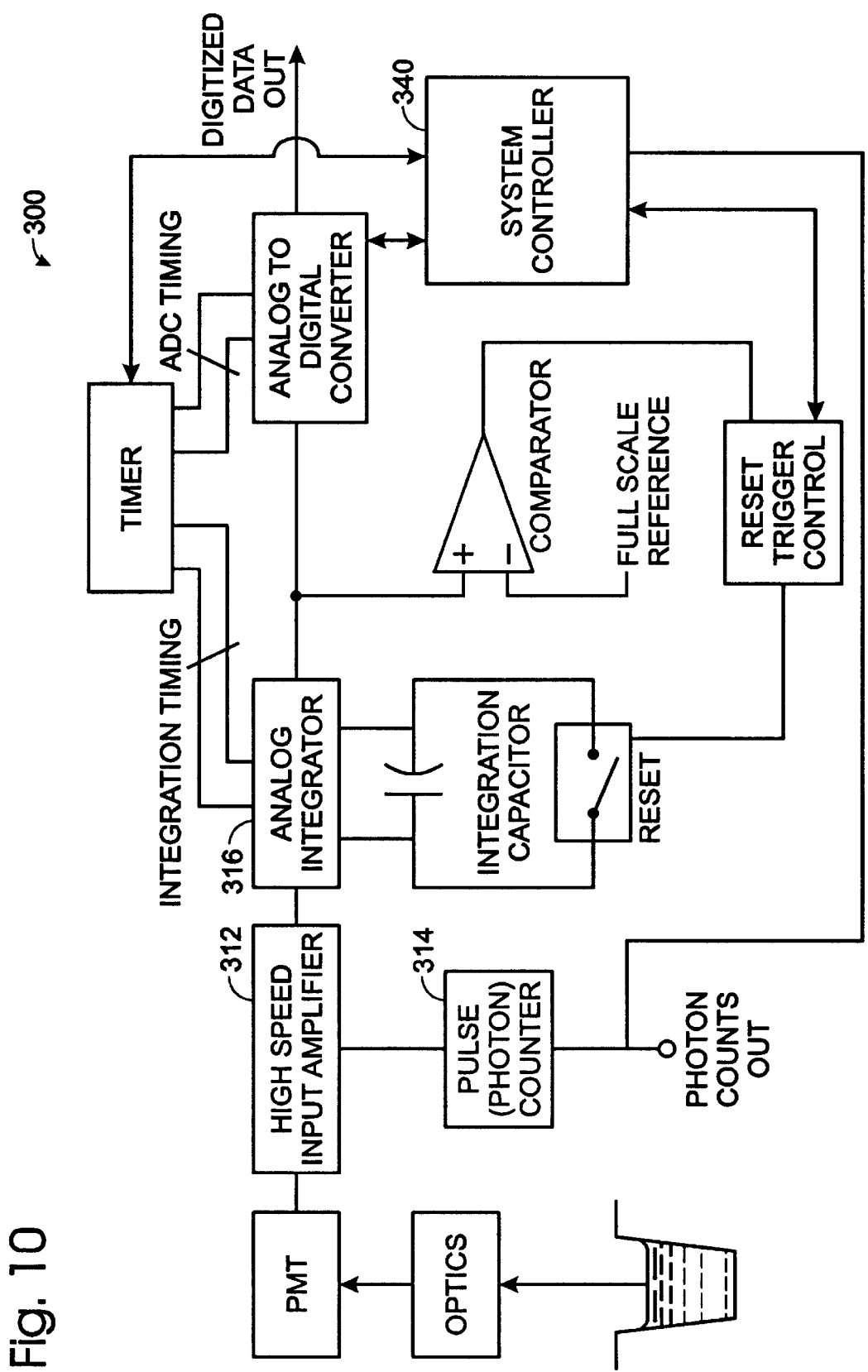
FIG. 10 is a block diagram of an alternative device for detecting light in accordance with the invention.

FIG. 10 is a block diagram showing an alternative device 300 for detecting light in accordance with the invention. Device 300 is similar to device 200 in FIG. 9, with a few exceptions. First, selector switch 212 in device 200 is replaced by a high-speed input amplifier 312 in device 300. High-speed input amplifier 312 should have accurate signal response from DC to 0.5 or 1 GHz AC to permit simultaneous use of a pulse counter 314 and an analog integrator 316. Second, output from the pulse counter in device 300 is connected to a system controller 340, unlike in device 200. Together, these differences extend the range of device 300 relative to device 200, because device 300 may automatically switch or choose between the pulse counter and the analog integrator, as received light levels and/or the system controller dictate.

The sampling or read time in devices 200 and 300 may be determined in at least two ways. First, the device may be instructed to integrate the detector output for a predetermined (fixed) time, as determined by the system controller and/or the timer. Second, the device may be instructed to integrate the detector output until a predetermined (fixed) integrated signal is obtained, as determined by the comparator and the value of the full scale reference.

Fixed-time and fixed-signal detection modes may be used to provide overflow protection and to extend dynamic range beyond that available with discrete or analog detection alone. In analog detection, information is lost if the integration capacitor or other storage component reaches its full-range value before the end of the sampling period, even though the PMT or other detector was not saturated. This is because the electronic circuit in analog counting cannot respond to signals above the full-scale count for each capacitor setting. With standard analog detection, each sample brighter than the saturation level will give an identical full-scale result.

The invention permits the intensity of detected light to be determined even if the integrated signal for the entire sample period would substantially exceed the storage capacity of the capacitor. The intensity of light may be expressed as an amount of light per unit time. In the invention, the time required to fully charge the storage component is measured by a timer operatively associated with the comparator. Thus, if the capacitor reaches full charge prior to the end of the sample period, intensity may be determined by relating the storage capacity of the capacitor to the amount of light detected by the detector, and then dividing that amount by the elapsed time in the sample period before reaching full charge. If the capacitor is not fully charged during the sampling period, then the intensity may be computed using the actual charge and the sampling period.

Fixed-time and fixed-signal detection modes also may be used to reduce read time and to provide underflow protection. Generally, optical assays are affected by various sources of error, including photon noise (PN) and pipetting error (PE), among others. The coefficient of variation (CV) associated with the results of an optical assay affected by such sources of error might be represented by the formula:

$$CV(assay)=[CV(PN)^2+CV(PE)^2]^{0.5} \tag{6}$$

where $CV(PN)=(\# \text{ detected photons})^{-0.5}$, and CV(PE) typically is in the range of 1–5%. Thus, to obtain a result that is limited by pipetting error, it is necessary only to collect enough photons to reduce CV(PN) to about 0.5–1%. This noise level corresponds to collecting between 10,000 and 20,000 photons. In many assays, good results may be obtained by collecting about this number of photons. For example, in fluorescence polarization assays, the polarization noise in milliPoise (mP) is given by:

$$\text{Polarization noise}=700/(\# \text{ detected photons})^{0.5} \tag{7}$$

Polarization assays generally require polarization noise to be less than 10 mP, corresponding to collecting at least about 5,000 photons.

Read time may be reduced by allowing the read time to vary as a function of signal strength, so that samples are analyzed just long enough to obtain a result that is not limited by the amount of light detected. For discrete detection, the pulse counter may be configured to count pulses only until a predetermined number or threshold of pulses is counted. For analog detection, the analog integrator may be configured to integrate the detector output until a preset threshold is achieved, where the threshold corresponds to collection of a predetermined amount of light. Specifically, the integrator may be zeroed, and the time required for the integrated detector current to trip the comparator may be measured. The integration time is a representation of the number of photons collected and hence the signal level.

The integrated detector current necessary to trip the comparator may be changed by changing the electronic gain, the threshold voltage, and/or the integration capacitor, among others. Such a change in comparator trip value will correspond to a chance in the number of photons that can be collected (and in the associated signal-to-noise value). To increase the number of photons collected, a larger capacitor and/or a lower gain may be employed. Conversely, to decrease the number of photons collected, a smaller capacitor and/or a shorter time-out period may be employed.

Generally, the desired amount of light (number of photons) will be acquired quickly if the sample is bright and slowly if the sample is dim. If the sample is so dim that the desired number of photons cannot be collected within a preset time limit or timeout period, an underflow occurs. In this case, the measurement is deemed to have "timed out," and the integrator voltage is measured by an analog-to-digital converter, or set to zero or another convenient value representing an underflow condition. Alternatively, if analog integration and photon-counting are performed simultaneously, the counter output determined in photon-counting mode may be used to determine intensity.

Table I shows the reduction in read times possible using variable-time reading, assuming that the reading time may be reduced from 100 milliseconds to 1 millisecond per sample. Reductions in read time become significant if numerous samples must be analyzed. For example, in high-throughput screening applications, samples may be housed in microplates that each contain 96, 384, or 1536 samples. Moreover, high-throughput screening applications typically require analyzing many such microplates.

TABLE I

| Plate Format | 96-well | 384-well | 1536-well |
| --- | --- | --- | --- |
| Move time + fixed read time | 43.2 sec | 115.2 sec | 307.2 sec |
| Move time + variable read time | 33.7 sec | 77.2 sec | 155.1 sec |
| Time saved per plate | 9.5 sec | 38.0 sec | 152.1 sec |
| Time savings (percent) | 23% | 33% | 49.5% |

The read time per microplate may be reduced using the savings in read time per sample, as shown in Table I. Alternatively, the read time per microplate may be held constant, independent of the read time per sample, if desired. The latter option may be useful if microplate analysis is coupled to other processes that occur at fixed time intervals.

Figure 11:
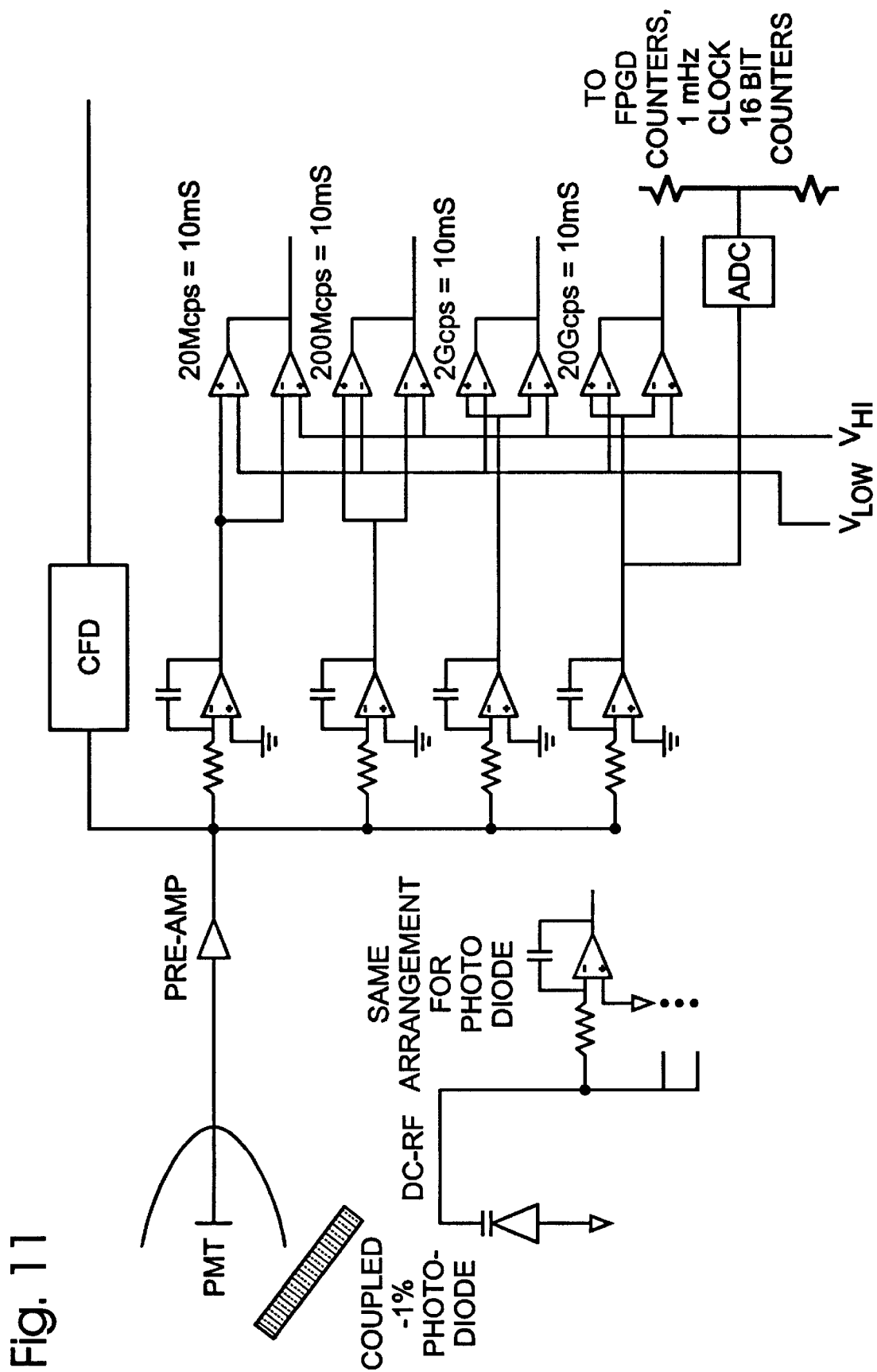
FIG. 11 is a schematic diagram of an integration section similar to those shown in FIGS. 9 and 10, except that it provides additional automatic range scaling.

FIG. 11 is a schematic diagram of an integration section similar to those shown in FIGS. 9 and 10, except that it provides additional automatic range scaling.

The signal output from the PMT is fed to a preamplifier that converts the current output from the PMT to a voltage output. As described above, this preamplifier should have good performance from DC to radio frequency AC.

The output of the preamplifier is fed in parallel to a number of integration devices. One integration device is a photon counter, which is useful for the lowest photon intensities. The other integration devices are four analog integrators, each having substantially identical construction, with the exception of the size of the integration capacitor. In particular, each of the first three analog integrators incorporates a capacitor that is about one order of magnitude smaller than the capacitor of the integrator that follows.

The output of each of the integration devices is fed to a discriminator section, which monitors the output voltage between a preselected high and low voltage, $V_L$ and $V_H$, as illustrated. The output of the individual discriminator sections for each integration device is used to trigger a counter corresponding to that integration device. The counter for each integration device begins counting when the output from the corresponding integration device exceeds $V_L$, and the counter stops counting when the output exceeds $V_H$. Thus, the counters can be used to determine the time required to saturate their associated integration devices. Thus, for a medium-intensity signal, the time required for the lowest range integration device to achieve saturation may be short relative to the overall sampling period. The time required for the next larger range integration device will be approximately an order of magnitude larger. The largest range integration devices may in fact not saturate during a particular sampling period with a medium intensity signal.

When computing a light intensity for a given sample period, it generally is preferable to select the output of an integration device that either recently saturated or was near to saturation. The signals from such devices, or the time required for saturation, as the case may be, will provide the most accurate basis for computing the intensity.

An advantage of this system is that an intensity value always can be computed based solely on the time to saturation for the largest range integration device that saturated. This can be accomplished by dividing the number of photons required for saturation by the time to saturation. If none of the analog integration devices saturated, the integrated signal from the counter can be used. Alternatively, the analog value of the integration device nearest to saturation but not having yet saturated can be measured with an analog-to-digital converter and utilized to compute the intensity.

To further increase the range of intensity that can be measured, an additional type of detector (e.g., photodiode) can be used in parallel with the PMT. The output of the photodiode can be fed to a series of analog integrators like those above. Thus, when the intensity exceeds that which accurately can be measured with a PMT, the photodiode will be in range.

As described above, the sample period may be terminated early if the user is satisfied when a predetermined number of photons are collected. Termination occurs when a corresponding integration signal has been achieved as measured by the integration devices.

Figure 12:
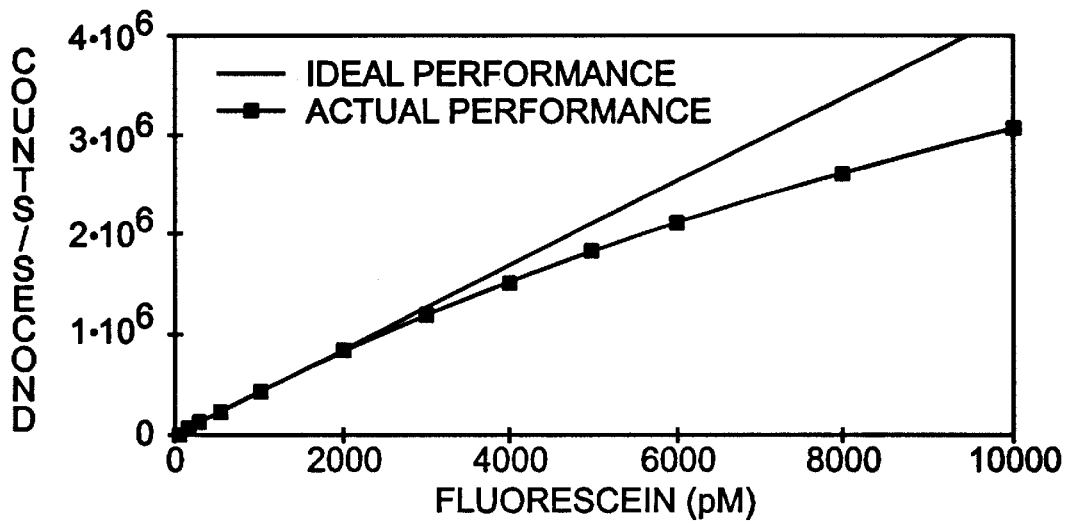
FIGS. 12 and 13 are response curves showing the non-linearity of the digital counting circuit for the apparatus shown in FIGS. 3–6.
Figure 13:
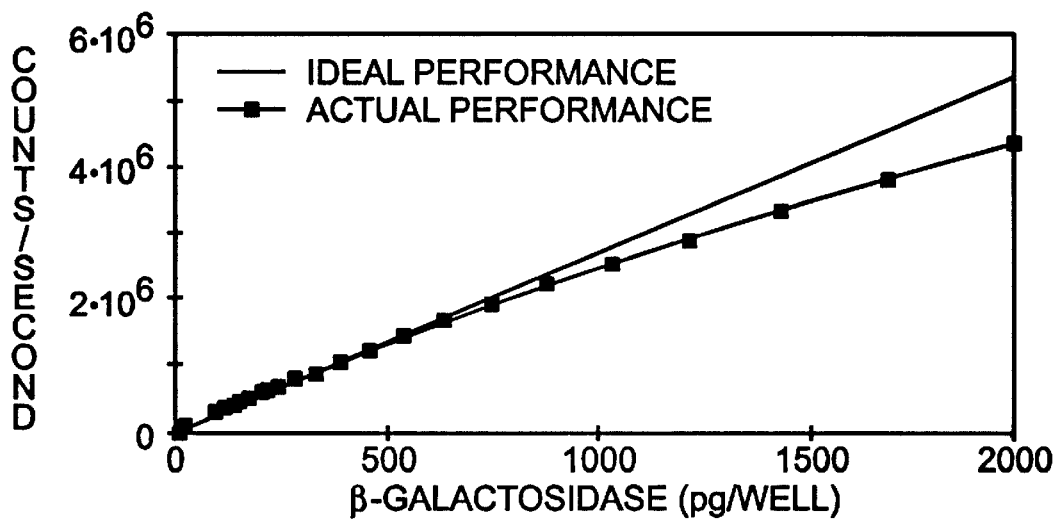

FIGS. 12 and 13 are response curves showing the non-linearity of the digital counting circuit for the apparatus shown in FIGS. 3–6. FIG. 12 was generated using the photoluminescence optical system, and shows a nonlinearity of 10% at 1.5 million counts/second, 15% at 2 million counts/second, 23% at 2.5 million counts/second, and 27% at 3 million counts/second. FIG. 13 was generated using the chemiluminescence optical system, and shows a nonlinearity of 5% at 2 million counts/second, 10% at 3 million counts/second, and 20% at 4 million counts/second.

Figure 14:
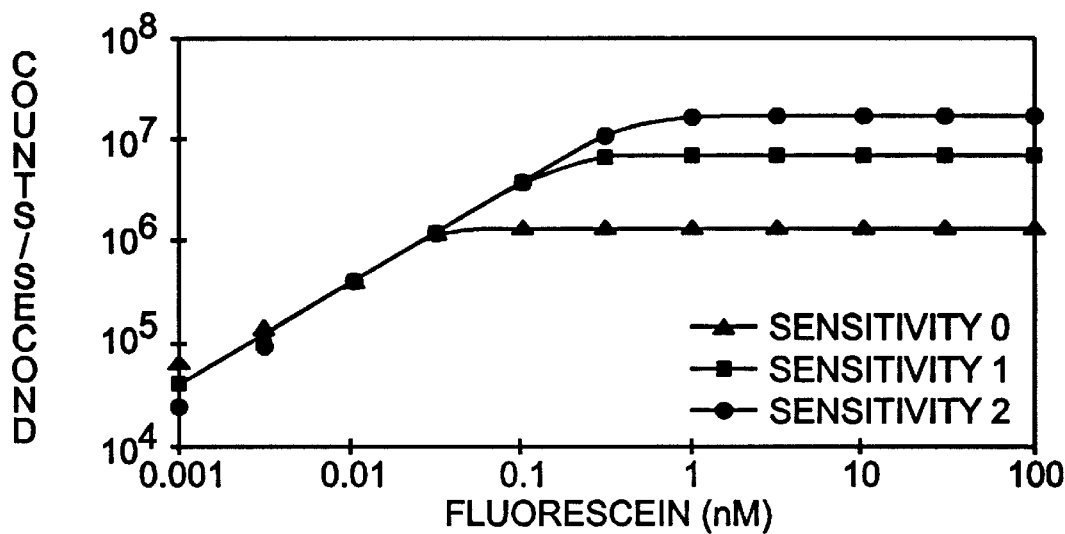
FIG. 14 is a response curve showing the saturation of the integrating capacitor in the analog counting circuit for the apparatus shown in FIGS. 3–6.

FIG. 14 is a response curve showing the saturation of the integrating capacitor in the analog counting circuit for the apparatus shown in FIGS. 3–6. The curves were generated using a 100 millisecond sampling period. Data are shown for three capacitors, including a relatively large capacitor (sensitivity 0) and a relatively small capacitor (sensitivity 2). The large capacitor saturates at higher light intensities than the small capacitor. The response for the largest capacitor is linear to about 10 million counts/second, which is about tenfold higher than with the digital counting circuit.

Figure 15:
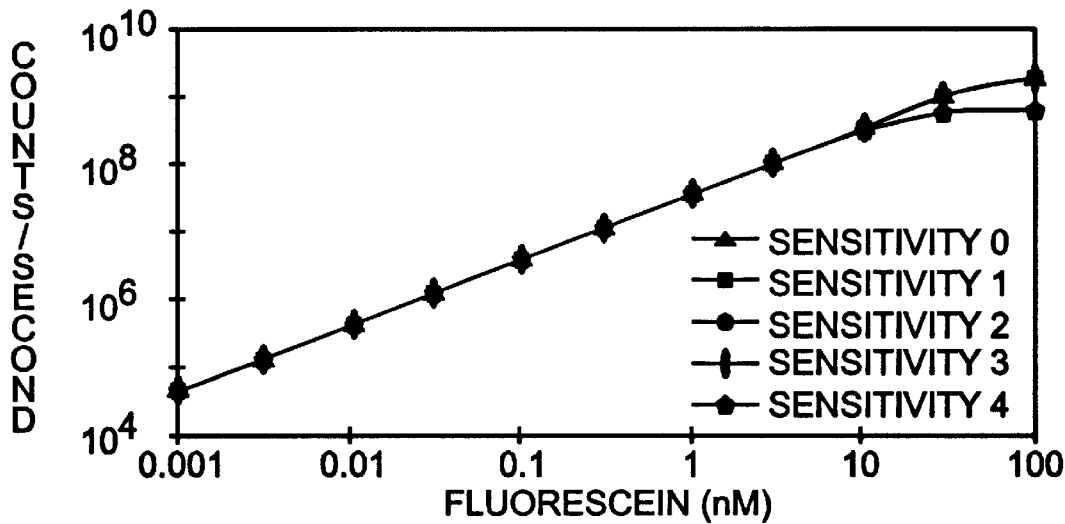
FIG. 15 is a response curve showing the saturation of the analog counting circuit when used with the comparator option for the apparatus shown in FIGS. 3–6.

FIG. 15 is a response curve showing the saturation of the analog counting circuit when used with the comparator option. FIG. 15 was generated using the same apparatus, sample, and 100 millisecond sampling period used in generating FIG. 14. The response is linear to about 1 billion counts/second, at least for the capacitors corresponding to sensitivities 0–3.

Table II shows guidelines for selecting appropriate counting options and units based on the assay, light source (if applicable), detector, and light intensity. These guidelines apply only to the embodiment shown in FIGS. 3–6 and 9, because they assume that there are separate chemiluminescence and photoluminescence optical systems, and that there is selectable photon counting or analog integration, with a comparator associated with the analog detection.

TABLE II

| | Discrete Counter | Analog Integrator | Comparator Option |
| --- | --- | --- | --- |
| Chemiluminescence | Optimal performance | Not applicable | Not applicable |
| Fluorescence Intensity (FI) (w/ continuous lamp) | Low level signals <1.0M cps | Higher signals or increase in dynamic range compared to | Optimal performance (with appropriate capacitor selection, |

TABLE II-continued

|  | Discrete Counter | Analog Integrator | Comparator Option |
|---|---|---|---|
| Units = cps |  | digital | good sensitivity and largest dynamic range) |
| Fluorescence Polarization (FP) (w/ continuous lamp) Units = cps | Low level signals <1.0M cps | Higher signals or increase in dynamic range compared to digital | Optimal performance (with appropriate capacitor selection, good sensitivity and largest dynamic range) |
| Time-Resolved Fluorescence (TRF) (w/ flash lamp) Units = counts or cps | Optimal performance Low signal levels <1.0M cps | Higher signals or increase in dynamic range (useful sensitivity settings 3 or 4) | Not recommended |
| Fluorescence intensity (w/ flash lamp) Units = counts | Not recommended (limited utility at the very lowest signal levels) | Optimal performance (with appropriate capacitor selection) | Not recommended |
| Fluorescence Polarization (w/ flash lamp) Units = counts | Not recommended (limited utility at the very lowest signal levels) | Optimal performance (with appropriate capacitor selection) | Not recommended |

Discrete (photon) counting sacrifices dynamic range for sensitivity at very low signal levels. Saturation (~1 million counts/second) is determined by the rate at which the detector and counting circuit receive photons. Optimal uses include low-intensity detection in chemiluminescence and time-resolved fluorescence assays.

Analog counting (PMT current integration) trades sensitivity at the lowest signal levels for increased dynamic range. Saturation occurs at much higher count rates (~0.5–1 billion counts/second) than with discrete counting. The maximum integrable signal usually is determined by the size of the integration capacitor. Optimal uses include fluorescence intensity and fluorescence polarization assays conducted using a flash lamp.

Comparator counting (analog+time to full scale) trades sensitivity at the lowest signal levels for the largest dynamic range with a single instrument setting. Saturation is similar to that stated for analog counting. In contrast to purely analog counting, at high signal levels the "comparator" circuit detects when the capacitor is fully charged and automatically measures the time taken for the capacitor to reach full scale. Optimal uses include low-intensity detection and dynamic range readings for fluorescence intensity and fluorescence polarization assays using a continuous lamp.

Although the invention has been disclosed in preferred forms, the specific embodiments thereof as disclosed and illustrated herein are not to be considered in a limiting sense, because numerous variations are possible. Applicants regard the subject matter of their invention to include all novel and nonobvious combinations and subcombinations of the various elements, features, functions, and/or properties disclosed herein. No single feature, function, element or property of the disclosed embodiments is essential. The following claims define certain combinations and subcombinations of features, functions, elements, and/or properties that are regarded as novel and nonobvious. Other combinations and subcombinations may be claimed through amendment of the present claims or presentation of new claims in this or a related application. Such claims, whether they are broader, narrower, or equal in scope to the original claims, also are regarded as included within the subject matter of applicants' invention.

We claim:

1. A system for determining the amount of light received by a detector during a sampling period, where the detector produces an output which is a function of light being received, the system comprising:

a first integration device operatively connected to the output of the detector and adapted to generate a first integration signal during the sampling period, the first integration signal being proportional to the amount of light received by the detector during the sampling period so long as the amount of light received during the sampling period is less than a first predetermined amount;

a second integration device operatively connected to the output of the detector and adapted to generate a second integration signal during the sampling period, the second integration signal being proportional to the amount of light received by the detector during the sampling period so long as the amount of light received during the sampling period is less than a second predetermined amount, wherein the second predetermined amount is at least several times greater than the first predetermined amount; and a range selection system connected to the first and second integration devices and configured to automatically select one of the integration signals to use in determining the amount of light received by the detector based upon the amount of light received during the sampling period as represented by the integration signals.

2. The system of claim 1, wherein the range selection system selects between the integrations signals based, at least in part, on whether the first integration signal exceeded the first predetermined amount during the sample period.

3. The system of claim 1, wherein the first integration device discretely counts pulses from the output of the detector corresponding to photons received by the detector.

4. The system of claim 1, wherein the first integration device carries out an analog integration corresponding to the output of the detector to generate the first integration signal.

5. The system of claim 1, further including a third integration device operatively connected to the output of the detector and adapted to generate a third integration signal during the sampling period, the third integration signal being proportional to the amount of light received by the detector during the sampling period so long as the amount of light received during the sampling period is less than a third predetermined amount, wherein the third predetermined amount is as least several times greater than the second predetermined amount.

6. The system of claim 1, further including a timer associated with the first integration device, the timer being configured to measure the time required for the first integration signal to reach a first threshold value.

7. A method of measuring light intensity from a source, comprising:

detecting photons incident on a detector from the source;

generating a first integration signal proportional to the cumulative number of photons incident on the detector during a sampling period so long as the cumulative number of photons is less than a first range value;

simultaneously with generating a first integration value, generating a second integration signal proportional to the number of photons incident on the detector during the sampling period so long as the cumulative number of photons is less than a second range value, where the second range value is at least an order of magnitude larger than the first range value;

selecting one of the integration signals to use in computing a detected light intensity based on whether the cumulative number of photons incident on the detector during the sampling period exceeded the first range value; and computing a detected light intensity using the selected integration signal.

8. The method of claim 7, further comprising simultaneously with generating first and second integration values, generating a third integration signal proportional to the number of photons incident on the detector during the sampling period so long as the cumulative number of photons is less than a third range value, where the third range value is at least an order of magnitude larger than the second range value.

* * * * *

UNITED STATES PATENT AND TRADEMARK OFFICE
CERTIFICATE OF CORRECTION

PATENT NO. : 6,326,605 B1
DATED : December 4, 2001
INVENTOR(S) : Douglas N. Modlin et al.

It is certified that error appears in the above-identified patent and that said Letters Patent is hereby corrected as shown below:

<u>Column 21,</u>
Line 5, delete "as", and insert -- at -- therefor.

Signed and Sealed this

Ninth Day of April, 2002

Attest:

JAMES E. ROGAN
*Director of the United States Patent and Trademark Office*

*Attesting Officer*